(12) United States Patent
Hussami et al.

(10) Patent No.: US 11,327,566 B2
(45) Date of Patent: May 10, 2022

(54) METHODS AND APPARATUSES FOR LOW LATENCY BODY STATE PREDICTION BASED ON NEUROMUSCULAR DATA

(71) Applicant: Facebook Technologies, LLC, Menlo Park, CA (US)

(72) Inventors: Nadine Hussami, Brooklyn, NY (US); Patrick Kaifosh, New York, NY (US); Alexandre Barachant, Brooklyn, NY (US); Daniel Wetmore, Brooklyn, NY (US)

(73) Assignee: Facebook Technologies, LLC, Menlo Park, CA (US)

( * ) Notice: Subject to any disclaimer, the term of this patent is extended or adjusted under 35 U.S.C. 154(b) by 229 days.

(21) Appl. No.: 16/833,309

(22) Filed: Mar. 27, 2020

(65) Prior Publication Data
US 2020/0310540 A1 Oct. 1, 2020

Related U.S. Application Data

(60) Provisional application No. 62/841,054, filed on Apr. 30, 2019, provisional application No. 62/826,516, filed on Mar. 29, 2019.

(51) Int. Cl.
*G06F 3/01* (2006.01)
*G06N 20/00* (2019.01)
(Continued)

(52) U.S. Cl.
CPC .............. *G06F 3/015* (2013.01); *G06F 3/017* (2013.01); *G06N 5/04* (2013.01); *G06N 20/00* (2019.01);
(Continued)

(58) Field of Classification Search
CPC .......... G06F 3/011; G06F 3/014; G06F 3/015; G06F 3/016; G06F 3/017; G06N 20/00;
(Continued)

(56) References Cited

U.S. PATENT DOCUMENTS

| 2013/0317648 A1* | 11/2013 | Assad ..................... G06F 3/014 700/258 |
| 2014/0198034 A1* | 7/2014 | Bailey ..................... G06F 3/016 345/156 |

(Continued)

OTHER PUBLICATIONS

International Search Report and Written Opinion received for PCT Application Serial No. PCT/US2020/025797 dated Jul. 9, 2020, 12 pages.

*Primary Examiner* — Afroza Chowdhury
(74) *Attorney, Agent, or Firm* — FisherBroyles, LLP

(57) ABSTRACT

The disclosed method may include receiving neuromuscular activity data over a first time series from a first sensor on a wearable device donned by a user receiving ground truth data over a second time series from a second sensor that indicates a body part state of a body part of the user, generating one or more training datasets by time-shifting at least a portion of the neuromuscular activity data over the first time series relative to the second time series, to associate the neuromuscular activity data with at least a portion of the ground truth data, and training one or more inferential models based on the one or more training datasets. Various other related methods and systems are also disclosed.

20 Claims, 14 Drawing Sheets

(51) Int. Cl.
*G06N 5/04* (2006.01)
*G16H 50/50* (2018.01)
*G16H 40/67* (2018.01)

(52) U.S. Cl.
CPC ............. *G16H 40/67* (2018.01); *G16H 50/50* (2018.01); *G06F 3/014* (2013.01)

(58) Field of Classification Search
CPC .......... G06N 3/0445; G06N 3/08; G06N 5/04; G16H 20/30; G16H 40/63; G16H 40/67; G16H 50/30; G16H 50/50
See application file for complete search history.

(56) References Cited

U.S. PATENT DOCUMENTS

| | | | |
|---|---|---|---|
| 2018/0024634 A1 | 1/2018 | Kaifosh et al. | |
| 2018/0024635 A1 | 1/2018 | Kaifosh et al. | |
| 2018/0081439 A1* | 3/2018 | Daniels | G06F 3/015 |
| 2018/0239430 A1* | 8/2018 | Tadi | H01L 33/58 |
| 2018/0301057 A1* | 10/2018 | Hargrove | A61B 5/681 |
| 2018/0307314 A1* | 10/2018 | Connor | G01R 27/02 |

* cited by examiner

METHODS AND APPARATUSES FOR LOW LATENCY BODY STATE PREDICTION BASED ON NEUROMUSCULAR DATA

CROSS REFERENCE TO RELATED APPLICATION

This application claims the benefit of U.S. Provisional Patent Application Ser. No. 62/826,516, titled "METHOD AND APPARATUS FOR LOW LATENCY HAND POSITION INFERENCE BASED ON NEUROMUSCULAR DATA," filed on Mar. 29, 2019, and U.S. Provisional Patent Application Ser. No. 62/841,054, titled "METHOD AND APPARATUS FOR LOW LATENCY HAND POSITION INFERENCE BASED ON NEUROMUSCULAR DATA," filed on Apr. 30, 2019, the disclosure of each of which is incorporated, in its entirety, by this reference.

BRIEF DESCRIPTION OF THE DRAWINGS

The accompanying drawings illustrate a number of example embodiments and are a part of the specification. Together with the following description, these drawings demonstrate and explain various principles of the present disclosure.

Figure 1:
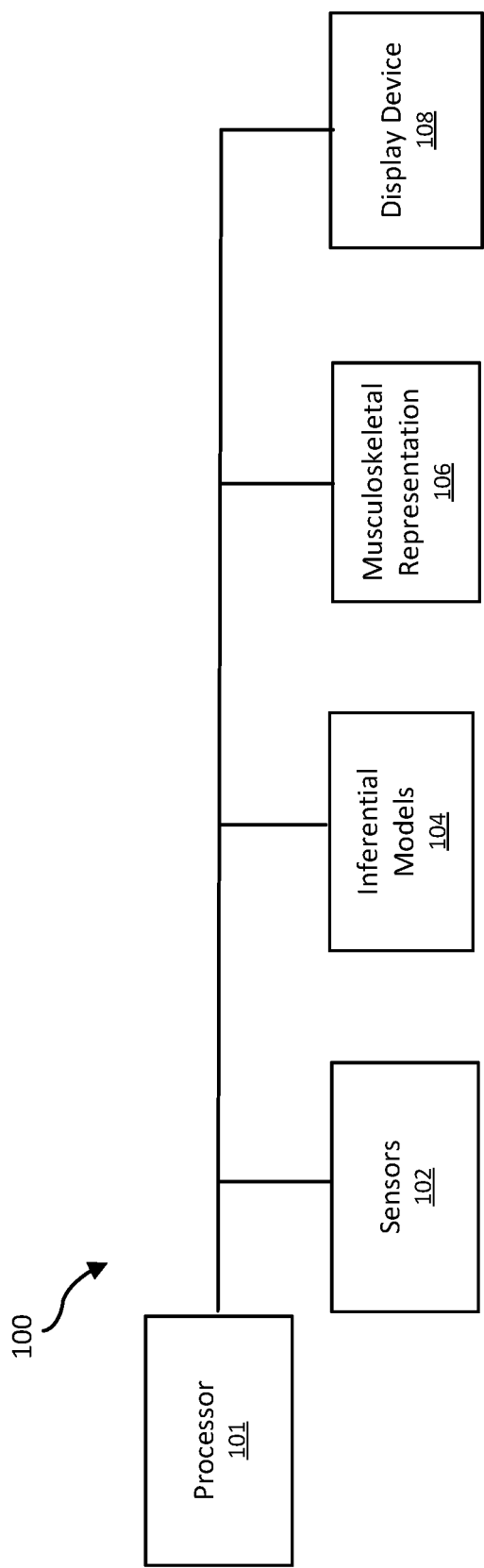
FIG. 1 is an illustration of an example block diagram of a system for predicting body state information, in accordance with embodiments of the present disclosure.

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the present disclosure covers all modifications, equivalents, and alternatives falling within the scope of the appended claims.

DETAILED DESCRIPTION OF EXAMPLE EMBODIMENTS

The present disclosure is generally directed to predicting body part states of a human user using trained inferential models. In some computer applications that generate musculoskeletal representations of the human body, it may be desirable for an application to know the spatial positioning, orientation, and movement of a user's body to provide a realistic representation of body movement to the application. For example, in an artificial-reality (AR) environment, tracking the spatial position of the user's hand may enable the application to accurately represent hand motion in the AR environment, which may allow the user to interact with (e.g., by grasping or manipulating) virtual objects within the AR environment. In a user interface application, detecting the presence or absence of a pose or gesture of the user may be used as a binary control input (e.g., mode switching) to a computer. An important feature of computer applications that generate musculoskeletal representations of the human body is low latency between a movement of the user's body and the representation of that movement by the computer application (e.g., displaying a visual representation to the user).

The time delay between onsets of neuromuscular activity (e.g., as indicated by electromyography (EMG) signals measured by a wearable device) and muscle contraction in a human body part may range from tens of milliseconds to hundreds of milliseconds or more, depending on physiological differences between individuals and the particular body part. Therefore, at any point in time, a neuromuscular activity signal corresponds to motion that may occur tens of milliseconds, or more, in the future.

Systems, methods, and apparatuses of the present disclosure for predicting a state of a body part, or a portion of a body part, based on neuromuscular activity data may achieve lower body state latency (e.g., the latency from recorded neuromuscular data to the output of a trained inferential model that predicts the state of the body part or the portion of the body part of the user) by temporally shifting neuromuscular activity signal data relative to ground truth measurements of body state. The temporally shifted data set may be used as an input for training an inferential model and/or as input to a previously trained inferential model.

In some embodiments, a method is provided that includes receiving neuromuscular activity signals in response to movement of a body part of a user via one or more neuromuscular sensors (e.g., neuromuscular sensors on a wearable device donned by the user), determining a ground truth (e.g., directly observed) measurement associated with a corresponding movement of the body part of the user, time shifting the neuromuscular activity signals to substantially align with a timing of the corresponding movement, and training an inferential model using the time shifted neuromuscular activity signals.

All or portions of the human musculoskeletal system may be modeled as a multi-segment articulated rigid body system, with joints forming the interfaces between the different segments and joint angles defining the spatial relationships between connected segments in the model. Constraints on the movement at the joints may be governed by the type of joint connecting the segments and the biological structures (e.g., muscles, tendons, ligaments, etc.) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion. A musculoskeletal representation may be a multi-segment articulated rigid body system used to model portions of the human musculoskeletal system. However, some segments of the human musculoskeletal system (e.g., the forearm), though approximated as a rigid body in the articulated rigid body system, may include multiple rigid structures (e.g., the ulna and radius bones of the forearm) that provide for more complex movement within the body segment that is not explicitly considered by rigid body models. Accordingly, a musculoskeletal representation may include body segments that represent a combination of body parts that are not strictly rigid bodies.

In some embodiments, a trained inferential model may be configured to predict a state of a portion of the body of a user. Such a body state may include a force, a movement, a pose, or a gesture of a body part or a portion of a body part. For example, the body state may include the positional relationships between body segments and/or force relationships for individual body segments and/or combinations of body segments in the musculoskeletal representation of the portion of the body of the user.

A predicted force may be associated with one or more segments of a musculoskeletal representation of the portion of the body of the user. Such predicted forces may include linear forces or rotational (e.g., torque) forces exerted by one or more segments of the musculoskeletal representation. Examples of linear forces include, without limitation, the force of a finger or a hand pressing on a solid object such as a table or a force exerted when two segments (e.g., two fingers) are squeezed together. Examples of rotational forces include, without limitation, rotational forces created when segments in the wrist and/or fingers are twisted and/or flexed. In some embodiments, the predicted body state may include, without limitation, squeezing force information, pinching force information, grasping force information, twisting force information, flexing force information, or information about co-contraction forces between muscles represented by the musculoskeletal representation.

A predicted movement may be associated with one or more segments of a musculoskeletal representation of the portion of the body of the user. Such predicted movements may include linear/angular velocities and/or linear/angular accelerations of one or more segments of the musculoskeletal representation. The linear velocities and/or the angular velocities may be absolute (e.g., measured with respect to a fixed frame of reference) or relative (e.g., measured with respect to a frame of reference associated with another segment or body part).

As used herein, the term "pose" may refer to a static configuration (e.g., the positioning) of one or more body parts. For example, a pose may include a fist, an open hand, statically pressing the index finger against the thumb, pressing the palm of a hand down on a solid surface, grasping a ball, or a combination thereof. As used herein, the term "gesture" may refer to a dynamic configuration of one or more body parts, the movement of the one or more body parts, forces associated with the dynamic configuration, or a combination thereof. For example, gestures may include waving a finger back and forth, throwing a ball, grasping a ball, or a combination thereof. Poses and/or gestures may be defined by an application configured to prompt a user to perform the pose and/or gesture. Additionally or alternatively, poses and/or gestures may be arbitrarily defined by a user.

In some embodiments, a body state may describe a hand of a user, which may be modeled as a multi-segment articulated body. The joints in the wrist and each finger may form the interfaces between the multiple segments in the model. In some embodiments, a body state may describe a combination of a hand with one or more arm segments of the user. The methods described herein are also applicable to musculoskeletal representations of portions of the body other than the hand including, without limitation, an arm, a leg, a foot, a torso, a neck, or a combination thereof.

Systems and methods of the present disclosure that compensate for electromechanical delay in the musculoskeletal system may achieve lower latency and/or increased accuracy in predicting body state as compared to traditional methods. Electromechanical delay in the musculoskeletal system may be defined as the time between the arrival of a motor neuron action potential at a neuromuscular synapse and force output (e.g., movement) of a part of the body directed by the motor neuron action potential. The time delay between onsets of neuromuscular activity (e.g., as indicated by EMG signals from a wearable device donned by the user) and muscle contraction may range from tens of milliseconds to more than hundreds of milliseconds, depending on the physiology of the user and the body part directed by the motor neuron action potential. Therefore, at any point in time, the EMG signals may correspond to motion of the body part that occurs tens of milliseconds, or more, in the future.

In some examples, an inferential model trained on neuromuscular signals temporally shifted relative to ground truth measurements of the body part state may evaluate the relationship between the neuromuscular signal and the body part's corresponding motion, rather than between the neuromuscular signal and motion corresponding to an earlier neuromuscular signal. Further, the introduction of this temporal shift may reduce the latency between the ground truth body state and the predicted body state output by the trained inferential model, thereby improving the user experience associated with the application (e.g., an artificial-reality application, a user interface application, etc.) because the body part representation (e.g., a visual representation on a head-mounted display) is more reactive to the user's actual motor control.

Electromechanical delays may vary between individuals and parts of a user's body (e.g., different delays for a hand vs. a leg due to their different sizes). In some examples, the amount that neuromuscular signals are shifted relative to ground truth data about the position of the arm, hand, wrist, and/or fingers may be optimized according to particular physiology shared between users (e.g., age or gender) or personalized for a specific user based on their personal electromechanical delay (e.g., for muscles of the forearm that control hand and finger movements). Training an inferential model using neuromuscular signals temporally shifted relative to ground truth measurements of the state may account for any or all factors known to influence electromechanical delays in the human neuromuscular system including, without limitation, body temperature, fatigue, circadian cycle, drug consumption, diet, caffeine consumption, alcohol consumption, gender, age, flexibility, muscle contraction level, or a combination thereof.

In some examples, an appropriate temporal shift may be identified by generating multiple training datasets with multiple temporal shifts. In some examples, the temporal shifts may be different respective time intervals. For example, a set of training datasets may be created with time intervals ranging from 5 ms to 100 ms in increments of 5 ms or from 10 ms to 150 ms in increments of 10 ms, or some other combination of starting time interval, ending time interval, and time increment. The multiple training datasets may be used to train multiple inferential models. The latency and accuracy of these models may then be assessed by comparing the models to the ground truth data. A model may be selected that exhibits a desired balance of latency and accuracy. The desired balance may depend on the task performed by the user. For example, a task prioritizing precise movement (e.g., tele-surgery) may accept greater latency in exchange for greater accuracy, while a task prioritizing rapid movement (e.g., a video game) may accept lower accuracy in exchange for lower latency.

In some examples, an inferential model trained using an appropriate delay time interval may be selected without generating multiple training datasets. For example, an inferential model may be trained using a known appropriate delay time interval. The known appropriate delay time interval may depend on a known electromechanical delay time and/or a known characteristic latency of the system. The known electromechanical delay time may be specific to a force, a movement, a pose, a gesture, a body part, a specific user, a user having a physiological characteristic (e.g., a specific age, sex, activity level, or other characteristic influencing electromechanical delays in the human neuromuscular system), or a combination thereof. The known electromechanical delay time may be directly determined by a clinician according to known methods for the particular user and/or estimated based on known electromechanical delay times for users sharing a physiological characteristic with the user.

In some examples, an appropriate delay time interval may be determined using a known electromechanical delay time for a body part, a user, and/or a category of users. For example, when the known electromechanical delay associated with the body part is 40 ms, the time intervals may be selected ranging from 20 to 60 ms. Prediction accuracies may be generated for inferential models trained using time-shifted training datasets generated using the selected time intervals. One or more of the inferential models may be selected for use in predicting body part state using the generated prediction accuracies. By selecting time intervals based on a known electromechanical delay time, the selection of the appropriate delay time interval may focus on time intervals likely to combine sufficient accuracy and low latency. As a result, fewer time intervals may be tested and/or a range of time intervals may be tested at a higher resolution (e.g., a 1 ms resolution rather than a 5 ms or a 10 ms resolution).

FIG. 1 illustrates a system 100 in accordance with embodiments of the present disclosure. The system 100 may include a plurality of sensors 102 configured to record signals resulting from the movement of portions of a human body. Sensors 102 may include autonomous sensors. In some examples, the term "autonomous sensors" may refer to sensors configured to measure the movement of body segments without requiring the use of external devices. In additional embodiments, sensors 102 may also include non-autonomous sensors in combination with autonomous sensors. In some examples, the term "non-autonomous sensors" may refer to sensors configured to measure the movement of body segments using external devices. Examples of non-autonomous sensors may include, without limitation, wearable (e.g., body-mounted) cameras, global positioning systems, laser scanning systems, radar ranging sensors, or a combination thereof.

Autonomous sensors may include a plurality of neuromuscular sensors configured to record signals arising from neuromuscular activity in muscles of a human body. The term "neuromuscular activity," as used herein, may refer to neural activation of spinal motor neurons that innervate a muscle, muscle activation, muscle contraction, or a combination thereof. Neuromuscular sensors may include one or more electromyography (EMG) sensors, one or more mechanomyography (MMG) sensors, one or more sonomyography (SMG) sensors, one or more sensors of any suitable type that are configured to detect neuromuscular signals, or a combination thereof. In some examples, sensors 102 may be used to sense muscular activity related to a movement of the body part controlled by muscles. Sensors 102 may be configured and arranged to sense the muscle activity. Spatial information (e.g., position and/or orientation information) and force information describing the movement may be predicted based on the sensed neuromuscular signals as the user moves over time.

Autonomous sensors may include one or more Inertial Measurement Units (IMUS), which may measure a combination of physical aspects of motion, using, for example, an accelerometer, a gyroscope, a magnetometer, or a combination thereof. In some examples, IMUs may be used to sense information about the movement of the body part on which the IMU is attached and information derived from the sensed data (e.g., position and/or orientation information) may be tracked as the user moves over time. For example, one or more IMUs may be used to track movements of portions of a user's body proximal to the user's torso (e.g., arms, legs) as the user moves over time.

Some embodiments may include at least one IMU and a plurality of neuromuscular sensors. The IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). Autonomous sensors may be arranged in any suitable way, and embodiments of the present disclosure are not limited to any particular sensor arrangement. For example, at least one IMU and a plurality of neuromuscular sensors may be co-located on a body segment to track movements of the body segment using different types of measurements. In some examples, an IMU sensor and a plurality of EMG sensors may be arranged on a wearable device configured to be worn around the lower arm (e.g., the forearm) or wrist of a user. In such an arrangement, the IMU sensor may be configured to track movement information (e.g., position, velocity, acceleration, and/or orientation over time) associated with one or more arm segments. The movement information may determine, for example, whether the user has raised or lowered their arm. The EMG sensors may be configured to determine movement information associated with wrist or hand segments to determine, for example, whether the user has an open or closed hand configuration.

Each of the autonomous sensors may include one or more sensing components configured to sense information about a user. In the case of IMUs, the sensing components may include one or more accelerometers, gyroscopes, magnetometers, or any combination thereof, to measure characteristics of body motion. Examples of characteristics of body motion may include, without limitation, acceleration, angular velocity, linear velocity, and sensed magnetic field around the body. The sensing components of the neuromuscular sensors may include, without limitation, electrodes configured to detect electric potentials on the surface of the body (e.g., for EMG sensors), vibration sensors configured to measure skin surface vibrations (e.g., for MMG sensors), acoustic sensing components configured to measure ultrasound signals (e.g., for SMG sensors) arising from muscle activity, or a combination thereof.

In some examples, the output of sensors 102 may be processed using hardware signal processing circuitry (e.g., to perform amplification, filtering, and/or rectification). In some examples, at least some signal processing of the output of sensors 102 may be performed in software. Thus, signal processing of autonomous signals recorded by the autonomous sensors may be performed in hardware, software, or by any suitable combination of hardware and software, as embodiments of the present disclosure are not limited in this respect.

In some examples, the recorded sensor data from sensors 102 may be processed to compute additional derived measurements that may be provided as input to an inferential models 104, as described in more detail below. For example, recorded signals from an IMU sensor may be processed to derive an orientation signal that specifies the orientation of a rigid body segment over time. Autonomous sensors may implement signal processing using components integrated with the sensing components or a portion of the signal processing may be performed by one or more components in communication with, but not directly integrated with, the sensing components of the autonomous sensors.

In some examples, the plurality of autonomous sensors may be arranged as a portion of a wearable device configured to be worn (e.g., donned) on or around part of a user's body. For example, an IMU sensor and/or a plurality of neuromuscular sensors may be arranged circumferentially around an adjustable and/or elastic band such as a wristband or armband that is configured to be worn around a user's wrist or arm. In some examples, an IMU sensor and/or a plurality of neuromuscular sensors may be arranged and/or attached to a portion and/or multiple portions of the body including, without limitation, an ankle, a waist, a torso, a neck, a head, a foot, a shin, a shoulder, or a combination thereof. Additionally or alternatively, the autonomous sensors may be arranged on a wearable patch configured to be affixed to a portion of the user's body. In some examples, multiple wearable devices, each having one or more IMUs and/or neuromuscular sensors included thereon, may be used to predict musculoskeletal position information for movements that involve multiple parts of the body.

In some examples, sensors 102 may only include a plurality of neuromuscular sensors (e.g., EMG sensors). In some examples, sensors 102 may include a plurality of neuromuscular sensors and at least one "auxiliary" or additional sensor configured to continuously record a plurality of auxiliary signals. Examples of auxiliary sensors may include, without limitation, other autonomous sensors such as IMU sensors, non-autonomous sensors such as imaging devices (e.g., a camera), radar ranging sensors, radiation-based sensors, laser-scanning devices, and/or other types of sensors such as heart-rate monitors.

System 100 also may include at least one processor 101 programmed to communicate with sensors 102. For example, signals recorded by one or more of sensors 102 may be provided to processor 101, which may be programmed to execute one or more machine learning algorithms that process signals output by sensors 102 to train one or more inferential models 104. The trained (or retrained) inferential models 104 may be stored for later use in generating a musculoskeletal representation 106, as described in more detail below. Non-limiting examples of inferential models 104 that may be used to predict body state information based on recorded signals from sensors 102 are discussed in detail below.

System 100 may include a display device 108 configured to display a visual representation of a body state (e.g., a visual representation of a hand). As discussed in more detail below, processor 101 may use one or more trained inferential models 104 configured to predict body state information based, at least in part, on signals recorded by sensors 102. The predicted body state information may be used to update musculoskeletal representation 106, which may be used to render a visual representation on display device 108 (e.g., a head-mounted display). Real-time reconstruction of the current body state and subsequent rendering of a visual representation on display device 108 reflecting the current body state information in the musculoskeletal model may provide visual feedback to the user about the effectiveness of inferential model 104 to accurately represent an intended body state. In some examples, a metric associated with musculoskeletal representation 106 (e.g., a likelihood metric for one or more hand gestures or a quality metric that represents a confidence level of estimating a position, movement, and/or force of a segment of a multi-segment articulated rigid body system such as a hand) may be provided to a user or other third-party.

In some examples, a computer application configured to simulate an artificial-reality environment may be instructed to display a visual representation of the user's hand on display device 108. Positioning, movement, and/or forces applied by portions of the hand within the artificial-reality environment may be displayed based on the output of the trained inferential model(s). The visual representation of the user's positioning, movement, and/or force may be dynamically (e.g., in real-time) updated based on current reconstructed body state information as signals are continuously recorded by sensors 102 and processed by trained inferential models 104.

As discussed above, some embodiments may be directed to using inferential models 104 for predicting musculoskeletal representation 106 based on signals recorded from sensors 102 (e.g., wearable autonomous sensors). Inferential models 104 may be used to predict the musculoskeletal position information without having to place sensors 102 on each segment of the rigid body that is to be represented in the computer-generated musculoskeletal representation 106. The types of joints between segments in a multi-segment articulated rigid body model may constrain movement of the rigid body. Additionally, different users may tend to move in individual ways when performing a task that may be captured in statistical patterns of individual user movement. At least some of these constraints on human body movement may be explicitly incorporated into inferential models 104 used for prediction. Additionally or alternatively, the constraints may be learned by inferential models 104 though training based on recorded data from sensors 102. Constraints imposed on the construction of inferential models 104 may be constraints set by the anatomy and physics of a user's body, while constraints derived from statistical patterns may be constraints set by human behavior for one or more users from which sensor measurements are recorded.

As discussed above, some embodiments may be directed to using inferential models 104 for predicting body state information to enable the generation and/or real-time update of a computer-based musculoskeletal representation 106. Inferential models 104 may be used to predict the body state information based on signals from sensors 102 including, without limitation, IMU signals, neuromuscular signals (e.g., EMG, MMG, and SMG signals), external device signals (e.g., camera, radar, or laser-scanning signals), or a combination thereof, as a user performs one or more movements.

Figure 2A:
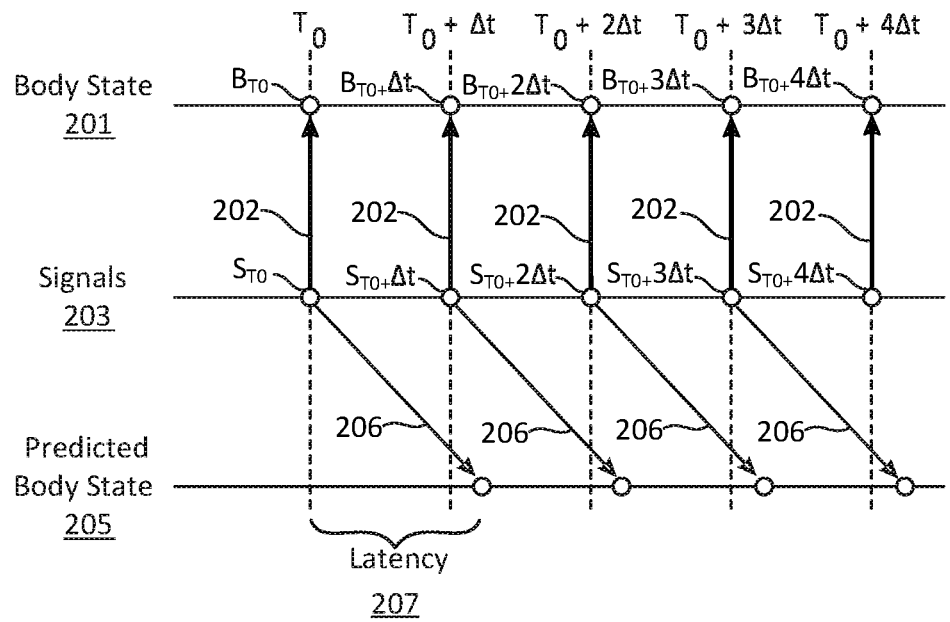
FIG. 2A is an illustration of an example chart depicting the effect of latency on predicting body state information, in accordance with embodiments of the present disclosure.

FIG. 2A illustrates an example chart depicting the effect of latency on predicting body state information, in accordance with embodiments of the present disclosure. A system may be configured to obtain repeated (e.g., periodic) measurements of neuromuscular signals 203 and body state 201 (e.g., ground truth body state) as a user performs one or more movements. For example, neuromuscular signals 203 and ground truth body state 201 may be time-series data (e.g., data recorded over a period of time), including explicitly and/or implicitly timestamped measurements (e.g., tuples of measurement value and measurement time, and/or a sequence of measurement values with a known sampling time interval and a known start time). The system may be configured to align samples of body state 201 and signals 203 based on acquisition time. The alignment of body state 201 and signals 203 samples may involve up-sampling, down-sampling, interpolation, other signal processing techniques, or a combination thereof. For example, the system may align body state samples $\{B_{T0}, B_{T0+\Delta t}, B_{T0+2\Delta t}, B_{T0+3\Delta t}, B_{T0+4\Delta t}, \ldots\}$ and signal samples $\{S_{T0}, S_{T0+\Delta t}, S_{T0+2\Delta t}, S_{T0+3\Delta t}, S_{T0+4\Delta t}, \ldots\}$ respectively as shown in FIG. 2A.

The system may be configured to train an inferential model(s) using body state 201 as ground truth data for signals 203. In some examples, the term "ground truth data" may be used interchangeably with the term "label time series data." Label time series data may be data collected over a period of time at a constant time interval or a variable time interval. A conventional system may be configured to predict the current body state sample using the current signal sample (e.g., predict $B_{T0}$ from $S_{T0}$ represented in FIG. 2A as arrow 202 connecting the signal sample to the body state at the same time). Due to electromechanical delay, the body state $B_{T0+\Delta t}$ may be the result of prior muscle activity. The body state $B_{T0+\Delta t}$ may therefore be more accurately predicted using an earlier signal sample (e.g., $S_{T0}$). Furthermore, prediction of body state from signal samples requires processing time. This processing time may include time delays associated with temporal integration of signals, signal recording and conditioning, transmission of signal data (e.g., from a wearable sensor to the processing system), memory access, processor instruction execution, and processing signal data using the inferential model. Such time delays may range between 10 ms and 100 ms, or greater.

Predicted body state 205 may depict when samples generated using signals 203 are output by the trained inferential model (as indicated by arrows 206 connecting samples of signals 203 with predicted body states 205). As shown in FIG. 2A, by the time the trained inferential model outputs predict body state $B_{T0}$, the most recently measured body part state may be $B_{T0+\Delta t}$. As used herein, latency may be a time period (e.g., an average time period, a median time period, or other suitable time period) between the measurement of a body state and the output of the corresponding predicted body state 205 (e.g., latency 207 between measured body state $B_{T0}$ and predicted body state $B_{T0}$). Latency may diminish the quality of the user experience, as a user may perceive the output of the system (e.g., a visual representation of the body state displayed on a head-mounted display (HMD)) to lag behind the user's actual movements.

Figure 2B:
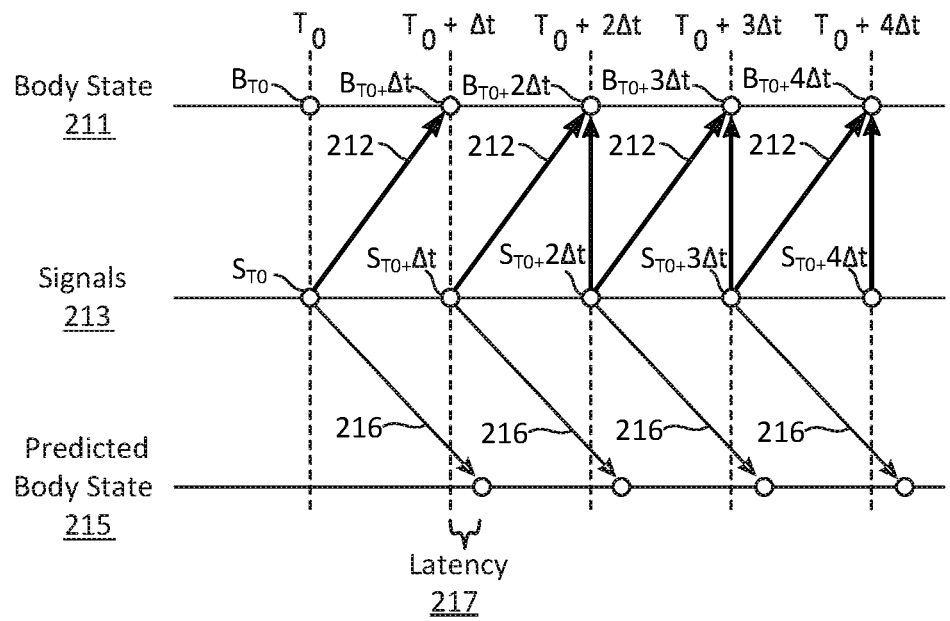
FIG. 2B is an illustration of an example chart depicting latency reduction in predicting body state information, in accordance with embodiments of the present disclosure.

FIG. 2B shows a chart depicting the effect on latency 217 of training an inferential model using time shifted training data, in accordance with embodiments of the present disclosure. As described above with reference to FIG. 2A, the system may obtain multiple samples of body state 211 (e.g., ground truth body state) and signals 213. In some examples, rather than pairing samples of signals 213 and body state 211 acquired at the same time, the system may be configured to pair samples of signals 213 with samples of body state 211 acquired at later times (as indicated by arrows 212 connecting samples of signals 213 with samples of body state 211). For example, the system may pair signal sample $S_{T0}$ with body state sample $B_{T0+\Delta t}$. In this manner, the system may create a training dataset by time-shifting either the signals 213 or the ground truth body state 211. The system may be configured to train an inferential model using the time-shifted training dataset. For example, the inferential model may then be trained to predict body state 211 from the signals 213 using the time-shifted training dataset.

Predicted body state 215 depicts when samples generated using signals 213 are output by the trained inferential model (as indicated by arrows 216 connecting samples of signals 213 with predicted body states 215). In this example, by the time the trained inferential model outputs predicted body state $B_{T0+\Delta t}$, the most recently measured body part state is also $B_{T0+\Delta t}$. As shown, latency 217 between when body state $B_{T0+\Delta t}$ occurs and when the trained inferential model outputs predicted body state $B_{T0+\Delta t}$ may be reduced compared to latency 207 shown in FIG. 2A by predicting $B_{T0+\Delta t}$ from $S_{T0}$. As discussed herein, the inferential model may be trained to predict $B_{T0+\Delta t}$ from $S_{T0}$ at least in part because electromechanical delay causes signals measured at time $T_0$ to affect later occurring body states (e.g., the body state at $T_{0+\Delta t}$). Thus, for an appropriate choice of delay time interval $\Delta t$, training the inferential model to predict $B_{T0+\Delta t}$ from $S_{T0}$ may improve body state prediction accuracy. Example methods for choosing delay time interval $\Delta t$ are discussed below with reference to FIGS. 3 and 4.

Figure 3:
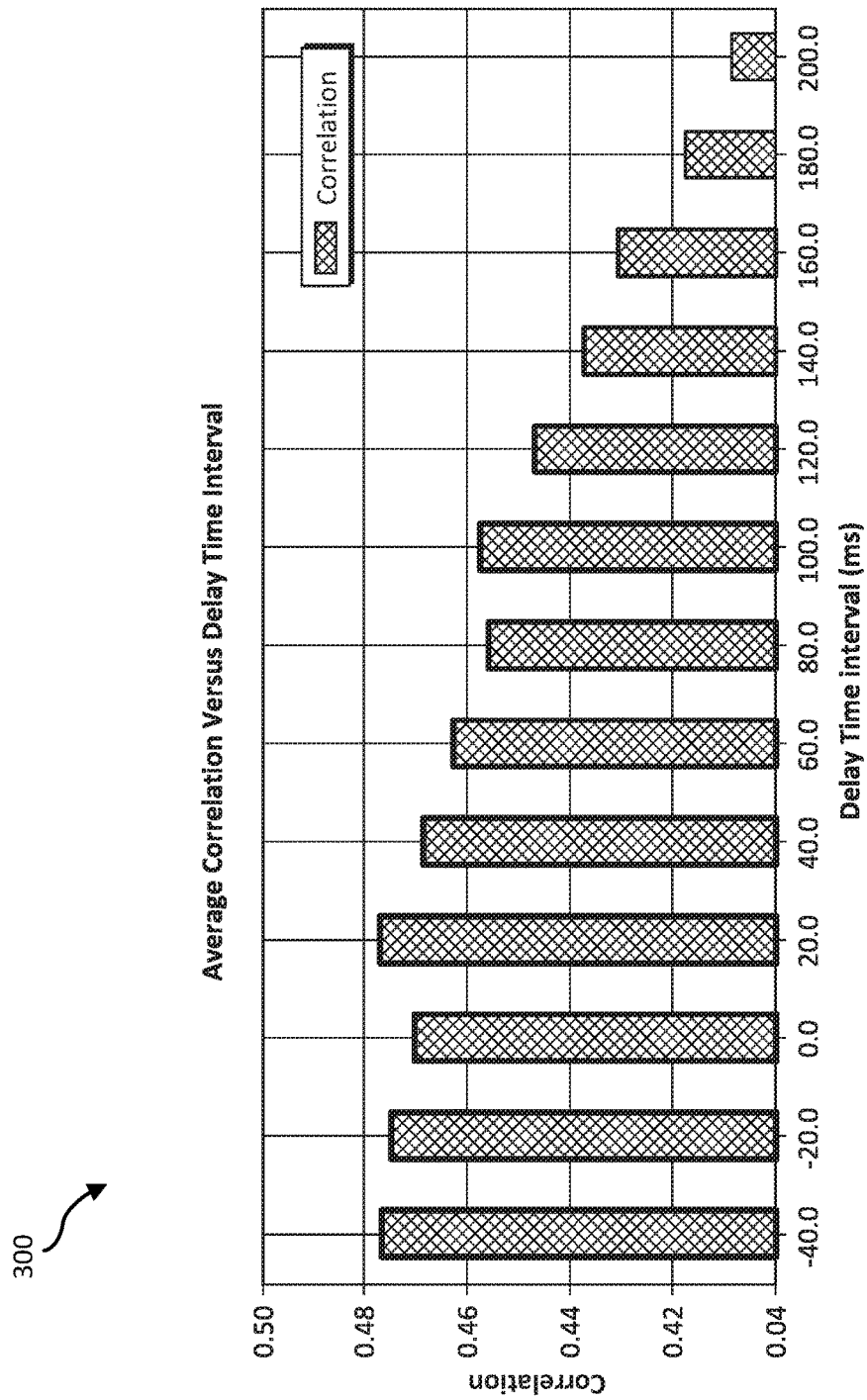
FIG. 3 is an illustration of an example chart depicting a relationship between delay time interval and body state prediction accuracy, in accordance with embodiments of the present disclosure.

FIG. 3 shows a chart 300 depicting an empirical relationship between delay time interval $\Delta t$ and body state prediction accuracy, in accordance with embodiments of present disclosure. The empirical relationship may be used to select a trained inferential model that exhibits a desired balance of latency and body state prediction accuracy. The independent variable depicted in FIG. 3 is the delay time interval between a neuromuscular signal sample and a body state sample. Positive time interval values correspond to pairing the neuromuscular signal sample with a body state sample obtained after the neuromuscular signal sample. Negative time interval values correspond to pairing the neuromuscular signal sample with a body state sample obtained before the neuromuscular signal sample. The zero time interval (0.0 ms) value corresponds to pairing the signal sample with a body state sample obtained at the same time as the signal sample. The response variable depicted in the chart of FIG. 3 may be a measure of the prediction accuracy of a model trained using a training dataset time-shifted by the time interval. The depicted measure may be a correlation value between measured and predicted joint angles in a musculoskeletal representation of a hand. In some examples, other measures of the prediction accuracy may be used, such as a mean squared error between characteristic values of a musculoskeletal representation of a body part. Such characteristic values may include, without limitation, joint angles, forces, or spatial coordinates of a body part. Similarly, a likelihood of correctly predicting a known pose or gesture (e.g., a first pose or transitioning from an open hand to a first pose) may be used as measure of the prediction accuracy. For example, the body part states and the predicted body part states may be binary labels indicating the presence or absence of a pose or gesture. The trained inferential model may have a false positive, false negative, true positive, or true negative prediction rate. The measure of prediction accuracy may depend on at least one of these prediction rates.

As shown in chart 300, body state prediction accuracy (e.g., correlation between measured and predicted joint angles) may improve as the delay time interval value increases from zero to 20 milliseconds. Prediction accuracy decreases thereafter as the delay time interval value increases. As shown, shifting the measured signals relative to the body state labels by 40 ms reduces latency without reducing prediction accuracy. As described herein, depending on the task, an inferential model trained using a shorter or longer time interval (e.g., a time interval in the range 10 to 100 ms) may be selected for use in predicting body state.

In some examples, an inferential model may be selected for use in predicting body state based on a prediction accuracy criterion (e.g., correlation between measured and predicted joint angles) and the delay time interval Δt used to generate the training dataset for training the inferential model. For example, of the inferential models satisfying a prediction accuracy criterion (e.g., accuracy above a set threshold), the selected inferential model may be the inferential model trained using the training dataset generated using the largest time interval. For example, two inferential models may satisfy the accuracy criterion (e.g., both models having an accuracy above an acceptable threshold). The first model may have greater accuracy than the second model, but the time interval used to generate the training dataset for training the first model may be less than the time interval used to generate the training dataset for training the second model. In this example, the second inferential model may be selected to predict the body state, as this second inferential model may have acceptable prediction accuracy and lower latency than the first inferential model.

The accuracy criterion may depend on the greatest accuracy observed across the inferential models. For example, the accuracy criterion may be expressed as a deviation from an accuracy of the most accurate model. When the deviation in accuracy for an inferential model is less than a threshold value, the inferential model may satisfy the accuracy criterion. The threshold value may be an absolute difference in accuracy (e.g., the most accurate model has a prediction accuracy of 85% and the second model has at least an accuracy of 80%). The threshold value may alternatively be a relative difference in accuracy (e.g., the less accurate model is at least 95% as accurate as the most accurate model).

Figure 4:
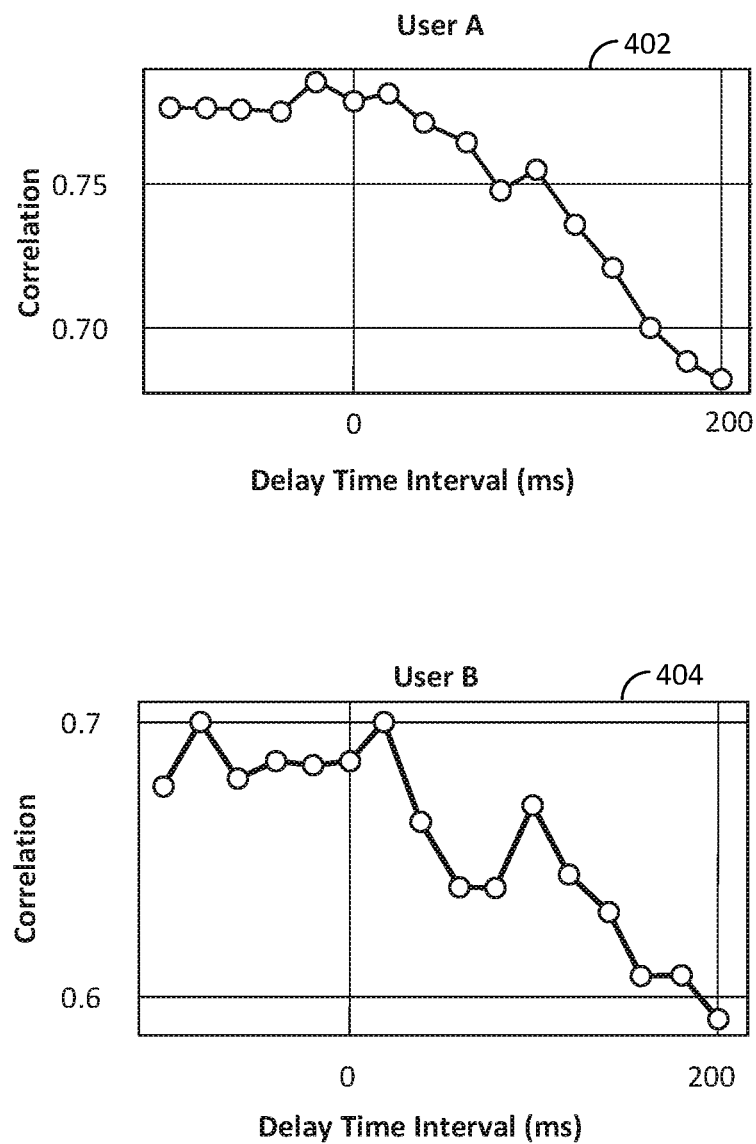
FIG. 4 illustrates two charts depicting user dependence in a relationship between delay time interval and body state prediction accuracy, in accordance with embodiments of the present disclosure.

FIG. 4 shows two charts depicting user dependence in the empirical relationship between time interval and prediction accuracy, in accordance with embodiments of the present disclosure. The dependence of prediction accuracy on delay time interval may vary between users. As shown in the charts of FIG. 4, the dependence of prediction accuracy on delay time interval may vary between user A as shown in chart 402 and user B as shown in chart 404. Accordingly, a system may be personalized to a user by selecting an inferential model trained using a delay time interval appropriate for the user and/or training an inferential model using a training dataset generated with a delay time interval appropriate for the user. The appropriate delay time interval may depend on a known electromechanical delay time and/or a characteristic latency of the system. For example, user A and user B may have different electromechanical delay times depending on physiological characteristics (e.g., user age, sex, activity level, or other characteristic known to influence electromechanical delays in the human neuromuscular system).

Figure 5:
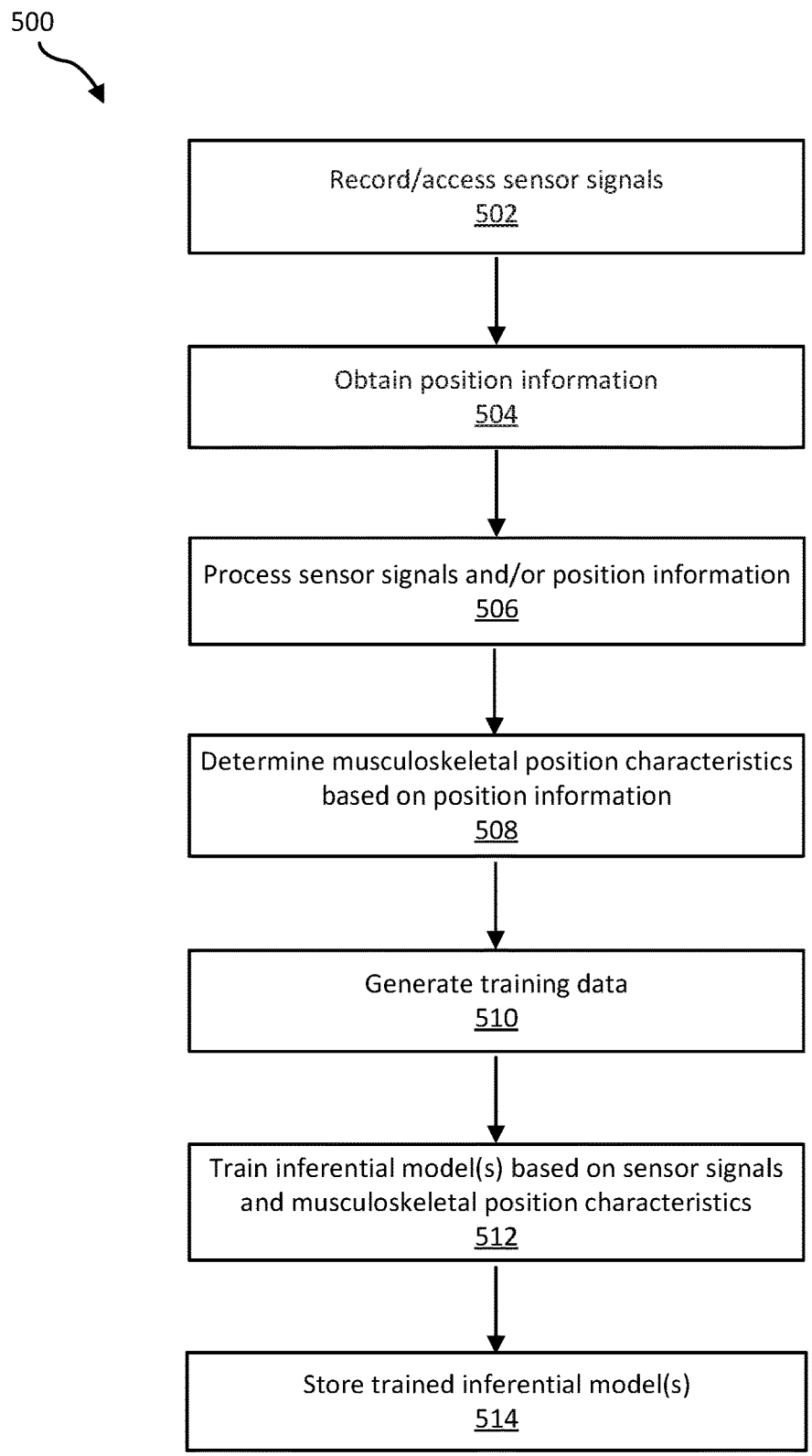
FIG. 5 is an illustration of a flowchart of an example method for generating an inferential model for predicting musculoskeletal position information using signals recorded from sensors, in accordance with embodiments of the present disclosure.

FIG. 5 describes a method 500 for generating (e.g., training) an inferential model using signals recorded from sensors (e.g., sensors 102). Method 500 may be executed using any suitable computing device(s), as embodiments of the present disclosure are not limited in this respect. For example, method 500 may be executed by one or more computer processors described with reference to FIGS. 1 and 7. As another example, one or more operations of method 500 may be executed using one or more servers (e.g., servers included as a part of a cloud computing environment). For example, at least a portion of the operations in method 500 may be performed using a cloud computing environment and/or a processor(s) of a wearable device such as wearable device 700 of FIG. 7, 810 of FIG. 8, 1100 of FIG. 11, 1200 of FIG. 12, 1320 of FIG. 13, 1404 of FIG. 14, or 1530 of FIG. 15. Although the operations of method 500 are shown in FIG. 5 as being performed in a certain order, the operations of method 500 may be performed in any order.

Method 500 may include operation 502, in which a plurality of sensor signals (e.g., neuromuscular signals, IMU signals, etc.) are obtained for one or more users performing one or more movements (e.g., playing an artificial-reality game). In some examples, the plurality of sensor signals may be recorded as part of method 500. Additionally or alternatively, the plurality of sensor signals may have been recorded prior to the execution of method 500 and are accessed (rather than recorded) at operation 502.

In some examples, the plurality of sensor signals may include sensor signals recorded for a single user performing a single movement and/or multiple movements. The user may be instructed to perform a sequence of movements for a particular task (e.g., grasping a game controller, providing a user input to a computer, etc.) and sensor signals corresponding to the user's movements may be recorded as the user performs the task that the user was instructed to perform. The sensor signals may be recorded by any suitable number and/or type of sensors located in any suitable location(s) to detect the user's movements that are relevant to the task performed. For example, after a user is instructed to perform a task with the fingers of the user's right hand, the sensor signals may be recorded by multiple neuromuscular sensors arranged (e.g., circumferentially) around the user's lower right arm to detect muscle activity in the lower right arm that causes the right hand movements and one or more IMU sensors arranged to predict the joint angle of the user's arm relative to the user's torso. As another example, after a user is instructed to perform a task with the user's leg (e.g., to kick an object), sensor signals may be recorded by multiple neuromuscular sensors arranged (e.g., circumferentially) around the user's leg to detect muscle activity in the leg that causes the movements of the foot and one or more IMU sensors arranged to predict the joint angle of the user's leg relative to the user's torso.

In some examples, the sensor signals obtained in operation 502 may correspond to signals from one type of sensor (e.g., one or more IMU sensors or one or more neuromuscular sensors) and an inferential model may be trained based on the sensor signals recorded using the particular type of sensor, resulting in a sensor-type specific trained inferential model. For example, the obtained sensor signals may include a plurality of EMG sensor signals arranged (e.g., circumferentially) around the lower arm or wrist of a user and the inferential model may be trained to predict musculoskeletal position information for movements of the wrist and/or hand during performance of a task such as grasping and turning an object such as a game controller or a doorknob.

In embodiments that provide predictions based on multiple types of sensors (e.g., IMU sensors, EMG sensors, MMG sensors, SMG sensors, etc.), a separate inferential model may be trained for each of the different types of sensors and the outputs of the sensor-type specific models may be combined to generate a musculoskeletal representation of the user's body. In some examples, the sensor signals obtained in operation 502 from two or more different types of sensors may be provided to a single inferential model that is trained based on the signals recorded from the different types of sensors. For example, an IMU sensor and a plurality of EMG sensors may be arranged on a wearable device configured to be worn around the forearm of a user, and signals recorded by the IMU and EMG sensors are collectively provided as inputs to an inferential model, as discussed in more detail below.

In some examples, a user may be instructed to perform a task multiple times and the sensor signals and position information may be recorded for each of multiple repetitions of the task by the user. In some examples, the plurality of sensor signals may include signals recorded for multiple users, each of the multiple users performing the same task one or more times. Each of the multiple users may be instructed to perform the task and sensor signals and position information corresponding to that user's movements may be recorded as the user performs (once or repeatedly) the task according to the instructions. When sensor signals are collected from multiple users and combined to generate an inferential model, an assumption may be made that different users employ similar musculoskeletal positions to perform the same movements. Collecting sensor signals and position information from a single user performing the same task repeatedly and/or from multiple users performing the same task one or multiple times facilitates the collection of sufficient training data to generate an inferential model that may accurately predict musculoskeletal position information associated with performance of the task.

In some examples, a user-independent inferential model may be generated based on training data corresponding to the recorded signals from multiple users, and as the system is used by a user, the inferential model may be trained based on recorded sensor data such that the inferential model learns the user-dependent characteristics to refine the prediction capabilities of the system and increase the prediction accuracy for the particular user.

In some examples, the plurality of sensor signals may include signals recorded for a user (or each of multiple users) performing each of multiple tasks one or multiple times. For example, a user may be instructed to perform each of multiple tasks (e.g., grasping an object, pushing an object, pulling open a door, etc.) and signals corresponding to the user's movements may be recorded as the user performs each of the multiple tasks the user(s) were instructed to perform. Collecting such signal data may facilitate developing an inferential model for predicting musculoskeletal position information associated with multiple different actions that may be performed by the user. For example, training data that incorporates musculoskeletal position information for multiple actions may facilitate generating an inferential model for predicting which of multiple possible movements a user may be performing.

As discussed above, the sensor data obtained at operation 502 may be obtained by recording sensor signals as each of one or multiple users perform each of one or more tasks one or more times. In operation 504, ground truth data (e.g., label time series data) may be obtained by multiple sensors including, without limitation, an optical sensor, an inertial measurement sensor, a mutual magnetic induction measurement sensor, a pressure sensor, or a combination thereof. The ground truth data may indicate a body part state of the user(s). For example, as the user(s) perform the task(s), position information describing the spatial position of different body segments during performance of the task(s) may be obtained in operation 504. In some examples, the position information may be obtained using one or more external devices or systems that track the position of different points on the body during performance of a task. For example, a motion capture system, a laser scanner, a device to measure mutual magnetic induction, some other system configured to capture position information, or a combination thereof may be used. As one non-limiting example, a plurality of position sensors may be placed on segments of the fingers of the hand of a user and a motion capture system may be used to determine the spatial location of each of the position sensors as the user performs a task such as grasping an object. Additionally or alternatively, neuromuscular signals may be obtained at operation 502 and may be used alone or in combination with one or more images from the motion capture system or IMU signals to determine the spatial location(s) of user body parts (e.g., fingers) as the user performs a task. The sensor data obtained at operation 502 may be recorded simultaneously with recording of the position information obtained in operation 504. In this example, the position information indicating the position of each finger segment over time as the grasping motion is performed is obtained.

Method 500 may proceed to operation 506, in which the sensor signals obtained in operation 502 and/or the position information obtained in operation 504 are optionally processed. For example, the sensor signals and/or the position information signals may be processed using, without limitation, amplification, filtering, rectification, other types of signal processing, or a combination thereof.

Method 500 may proceed to operation 508, in which musculoskeletal position characteristics are determined based on the position information (as collected in operation 504). In some examples, rather than using recorded spatial (e.g., x, y, z) coordinates corresponding to the position sensors as training data to train the inferential model, a set of derived musculoskeletal position characteristic values are determined based on the recorded position information, and the derived values are used as training data for training the inferential model. For example, using information about constraints between connected pairs of rigid segments in the articulated rigid body model, the position information may be used to determine joint angles between each connected pair of rigid segments at each of multiple time points during performance of a task. Accordingly, the position information obtained in operation 504 may be represented by a vector of n joint angles at each of a plurality of time points, where n is the number of joints or connections between segments in the articulated rigid body model.

Method 500 may proceed to operation 510, in which the time series information obtained at operations 502 and 508 may be combined to create training data used for training an inferential model. The obtained data may be combined using any suitable method. In some examples, each of the sensor signals obtained at operation 502 may be associated with a task or movement within a task corresponding to the musculoskeletal position characteristics (e.g., joint angles) determined based on the positional information obtained in operation 504 as the user performed the task or movement. In this way, the sensor signals may be associated with musculoskeletal position characteristics (e.g., joint angles) and the inferential model may be trained to predict that the musculoskeletal representation will be characterized by particular musculoskeletal position characteristics between different body segments when particular sensor signals are recorded during performance of a particular task.

In embodiments including sensors of different types (e.g., IMU sensors and neuromuscular sensors) that are configured to simultaneously record different types of movement information (e.g., position information, velocity information, acceleration information) during performance of a task, the sensor data for the different types of sensors may be recorded using the same or different sampling rates. When the sensor data is recorded at different sampling rates, at least some of the sensor data may be resampled (e.g., up-sampled or down-sampled) such that all sensor data provided as input to the inferential model corresponds to time series data at the same time resolution (e.g., the time period between samples). Resampling at least some of the sensor data may be performed using any suitable method including, without limitation, using interpolation for up-sampling sensor data and using decimation for down-sampling sensor data.

Additionally or alternatively, some embodiments may employ an inferential model configured to accept multiple inputs asynchronously. For example, the inferential model may be configured to model the distribution of the "missing" values in the input data having a lower sampling rate. Additionally or alternatively, the timing of training of the inferential model may occur asynchronously as input from multiple sensor data measurements becomes available (e.g., after signal conditioning) as training data.

Combining the time series information obtained at operations 502 and 508 to create training data for training an inferential model at operation 510 may include generating one or more training datasets. As described herein, the one or more training datasets may be generated by time-shifting the sensor signals obtained at operation 502 or by time-shifting the ground truth data obtained at operation 504 or 508 by one or more time intervals.

Method 500 may proceed to operation 512, in which an inferential model for predicting musculoskeletal position information may be trained using the training data generated at operation 510. The inferential model being trained may use a sequence of data sets as an input, and each of the data sets in the sequence may include an n-dimensional vector of sensor data. The inferential model may provide output that indicates, for each of one or more tasks or movements that may be performed by a user, the likelihood that the musculoskeletal representation of the user's body will be characterized by a set of musculoskeletal position characteristics (e.g., a set of joint angles between segments in an articulated multi-segment body model). For example, the inferential model may use as input a sequence of vectors $\{x_k | 1 \leq k \leq K\}$ generated using measurements obtained at time points t1, t2, . . . , tK, where the ith component of vector xj may be a value measured by the ith sensor at time tj and/or derived from the value measured by the ith sensor at time tj. In another non-limiting example, a derived value provided as input to the inferential model may include features extracted from the data for all, or a subset of, the sensors at and/or prior to time tj (e.g., a covariance matrix, a power spectrum, any other suitable derived representation, or a combination thereof). Based on such input, the inferential model may provide output indicating a probability that a musculoskeletal representation of the user's body will be characterized by a set of musculoskeletal position characteristics. As one non-limiting example, the inferential model may be trained to predict a set of joint angles for segments in the fingers of a hand over time as a user grasps an object. In this example, the trained inferential model may output, a set of predicted joint angles for joints in the hand corresponding to the sensor input.

In some examples, the inferential model may be a neural network. In some examples, the inferential model may be a recurrent neural network. The recurrent neural network may be a long short-term memory (LSTM) neural network. However, the recurrent neural network is not limited to an LSTM neural network and may have any other suitable architecture. For example, the recurrent neural network may be, without limitation, a fully recurrent neural network, a recursive neural network, a variational autoencoder, a Hopfield neural network, an associative memory neural network, an Elman neural network, a Jordan neural network, an echo state neural network, a second order recurrent neural network, any other suitable type of recurrent neural network, or a combination thereof. In some examples, neural networks that are not recurrent neural networks may be used. For example, deep neural networks, convolutional neural networks, feedforward neural networks, or a combination thereof may be used.

In some examples in which the inferential model is a neural network, the output layer of the neural network may provide a set of output values corresponding to a respective set of possible musculoskeletal position characteristics (e.g., joint angles). In this example, the neural network may operate as a non-linear regression model configured to predict musculoskeletal position characteristics from raw and/or processed (e.g., conditioned) sensor measurements. In some examples, other suitable non-linear regression models may be used instead of a neural network, as the present disclosure is not limited in this respect.

In some examples, the neural network may be implemented based on multiple and/or different types of topologies and/or architectures including deep neural networks with fully connected (e.g., dense) layers, Long Short-Term Memory (LSTM) layers, convolutional layers, Temporal Convolutional Layers (TCL), other suitable types of deep neural network topology and/or architectures, or a combination thereof. The neural network may have different types of output layers including, without limitation, output layers with logistic sigmoid activation functions, hyperbolic tangent activation functions, linear units, rectified linear units, other suitable types of nonlinear units, or a combination thereof. In some examples, the neural network may be configured to represent the probability distribution over n different classes via a softmax function. In some examples, the neural network may include an output layer that provides a parameterized distribution (e.g., a mean and/or a variance of a Gaussian distribution).

Embodiments of the present disclosure are not limited to using neural networks as other types of inferential models may be employed. In some examples, the inferential model may include, without limitation, a hidden Markov model, a Markov switching model that allows switching among different dynamic systems, dynamic Bayesian networks, any other suitable graphical model having a temporal component, or a combination thereof. Any such inferential model may be trained at operation 512 using the sensor data obtained at operation 502.

As another example, the inferential model may use as input features derived from the sensor data obtained at operation 502. In such embodiments, the inferential model may be trained at operation 512 using features extracted from the sensor data obtained at operation 502. The inferential model may include, without limitation, a support vector machine, a Gaussian mixture model, a regression-based classifier, a decision tree classifier, a Bayesian classifier, any other suitable classifier, or a combination thereof. Input features to be provided as training data to the inferential model may be derived from the sensor data obtained at operation 502 using any suitable method. For example, the sensor data may be analyzed as time series data using, without limitation, wavelet analysis techniques (e.g., a continuous wavelet transform, a discrete-time wavelet transform, etc.), Fourier-analysis techniques (e.g., short-time Fourier transform, discrete-time Fourier transform, Fourier transform, etc.), any other suitable type of time-frequency analysis technique, or a combination thereof. As one non-limiting example, the sensor data may be transformed using a wavelet transform and the resulting wavelet coefficients may be provided as inputs to the inferential model.

In some examples, at operation 512, values for parameters of the inferential model may be estimated from the training data generated at operation 510. For example, when the inferential model is a neural network, parameters of the neural network (e.g., weights) may be estimated from the training data. Parameters of the inferential model may be estimated using, without limitation, gradient descent, stochastic gradient descent, any other suitable iterative optimization technique, or a combination thereof. In embodiments in which the inferential model is a recurrent neural network (e.g., an LSTM neural network), the inferential model may be trained using stochastic gradient descent and backpropagation through time. The training may employ a cross-entropy loss function and/or any other suitable loss function, as the present disclosure is not limited in this respect.

Method 500 may proceed to operation 514, in which the trained inferential model may be stored (e.g., in a datastore, a local database, a remote cloud database, a memory, etc.). The trained inferential model may be stored using any suitable format, device(s) and/or method. In this way, the inferential model generated during execution of method 500 may be used at a later time. For example, a state prediction system may be configured using the trained inferential model to predict body part state from neuromuscular activity time series data (e.g., predict musculoskeletal position information such as joint angles from a given set of input sensor data), as described below.

In some examples, sensor signals may be recorded from a plurality of sensors (e.g., arranged on or near the surface of a user's body) that record activity associated with movements of the body during performance of a task. The recorded signals may be optionally processed (e.g., conditioned) and provided as input to an inferential model trained using one or more techniques described above in reference to FIG. 5. In some examples, autonomous signals may be continually recorded, and the continuously recorded signals (raw or processed) may be continuously and/or periodically provided as input to the trained inferential model for prediction of musculoskeletal position information (e.g., joint angles) for the given set of input sensor data. As discussed above, in some examples, the trained inferential model may be a user-independent model trained based on autonomous sensor and position information measurements from a plurality of users. In some examples, the trained model may be a user-dependent model trained on data recorded from the individual user from which the data associated with the sensor signals is also acquired.

After the trained inferential model receives the sensor data as a set of input parameters, the predicted musculoskeletal position information may be output from the trained inferential model. As discussed above, in some examples, the predicted musculoskeletal position information may include a set of musculoskeletal position information values (e.g., a set of joint angles) for a multi-segment articulated rigid body model representing at least a portion of the user's body. In some examples, the musculoskeletal position information may include a set of probabilities that the user is performing one or more movements from a set of possible movements.

In some examples, after musculoskeletal position information is predicted, a computer-based musculoskeletal representation of the user's body may be generated based, at least in part, on the musculoskeletal position information output from the trained inferential model. The computer-based musculoskeletal representation may be generated using any suitable method. For example, a computer-based musculoskeletal model of the human body may include multiple rigid body segments, each of which corresponds to one or more skeletal structures in the body. For example, the upper arm may be represented by a first rigid body segment, the lower arm may be represented by a second rigid body segment, the palm of the hand may be represented by a third rigid body segment, and each of the fingers on the hand may be represented by at least one rigid body segment. A set of joint angles between connected rigid body segments in the musculoskeletal model may define the orientation of each of the connected rigid body segments relative to each other and a reference frame, such as the torso of the body. As new sensor data is measured and processed by the inferential model to provide new predictions of the musculoskeletal position information (e.g., an updated set of joint angles), the computer-based musculoskeletal representation of the user's body may be updated based on the updated set of joint angles determined based on the output of the inferential model. In this way, the computer-based musculoskeletal representation may be dynamically updated in real-time as sensor data is continuously recorded.

The computer-based musculoskeletal representation may be represented and stored using any suitable devices and methods. For example, the computer-based musculoskeletal representation may be stored in memory (e.g., memory 821 of FIG. 8). Although referred to herein as a "musculoskeletal" representation to reflect that muscle activity may be associated with the representation, some musculoskeletal representations may correspond to skeletal structures, muscular structures, or a combination of skeletal structures and muscular structures in the body.

In some examples, direct measurement of neuromuscular activity and/or muscle activity underlying the user's movements may be combined with the generated musculoskeletal representation. Measurements from a plurality of sensors placed on a user's body may be used to create a unified representation of muscle recruitment by superimposing the measurements onto a dynamically-posed skeleton. In some examples, muscle activity sensed by neuromuscular sensors and/or information derived from the muscle activity (e.g., force information) may be combined with the computer-generated musculoskeletal representation in real time.

Figure 6:
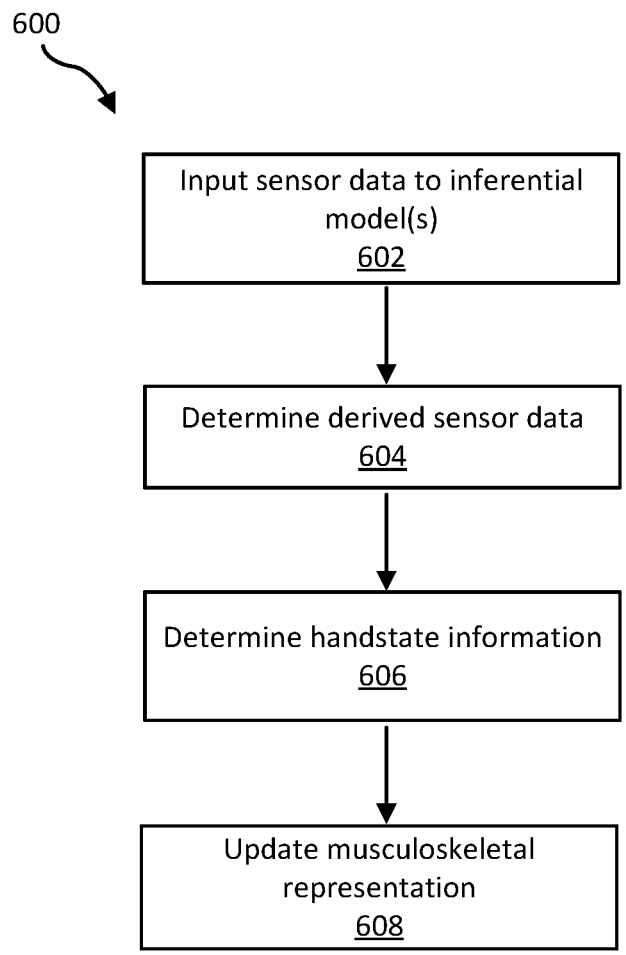
FIG. 6 is an illustration of a flowchart of an example method for determining body state information, in accordance with embodiments of the present disclosure.

FIG. 6 illustrates a method 600 for determining body state information based on recorded sensor data in accordance embodiments of the present disclosure. Although the operations of method 600 are shown in FIG. 6 as being performed in a certain order, the operations of method 600 may be performed in any order. In operation 602, sensor data may be recorded by one or more sensors and provided as input to one or more trained inferential models used to predict a body state, as described above. In some examples, the sensors may include a plurality of neuromuscular sensors (e.g., EMG sensors) arranged on a wearable device worn by a user. For example, EMG sensors may be arranged (e.g., circumferentially) on an elastic band configured to be worn around a wrist or forearm of the user to record neuromuscular signals from the user as the user exerts force and/or performs various movements, poses, and/or gestures. Examples of wearable devices that may be used in accordance with embodiments of the present disclosure include wearable device 700 of FIG. 7, 800 of FIG. 8, 1320 of FIG. 13, 1404 of FIG. 14, or 1530 of FIG. 15, which are described in more detail below.

Additionally or alternatively, some embodiments may include one or more auxiliary sensors configured to continuously record auxiliary signals that may also be provided as input to the one or more trained inferential models. Examples of auxiliary sensors may include, without limitation, IMU sensors, imaging devices, radiation detection devices (e.g., laser scanning devices), heart rate monitors, any other type of biosensors configured to continuously record biophysical information from the user during performance of one or more movements or gestures, or a combination thereof.

Method 600 may proceed to operation 604, in which derived signal data is optionally determined based on the signals recorded by the sensors. For example, accelerometer data recorded by one or more IMU sensors may be integrated and/or filtered to determine derived signal data associated with one or more muscles during performance of a gesture. The derived signal data may be provided as input to the trained inferential model(s) in addition to, or as an alternative to, raw signal data or otherwise processed raw signal data recorded by the sensors.

Method 600 may proceed to operation 606, in which body state information is determined based on the output of the trained inferential model(s). Gestures performed by the user may include discrete gestures, such as placing the user's hand palm down on a table, and/or continuous movement gestures, such as waving a finger back and forth. The neuromuscular signals may be recorded continuously during user movements including during performance of the gesture and may be provided continuously as input to the trained inferential model, resulting in real-time estimation of the positions and/or forces of the user's body part (e.g., body state information) as output of the trained inferential model(s). Method 600 may proceed to operation 608, in which the real-time body state predictions output from the trained inferential model(s) are used to update a musculoskeletal representation associated with a hand. In some examples, the musculoskeletal representation represents rigid segments within a hand and the joints connecting the rigid segments. In other embodiments, the musculoskeletal representation may include at least some rigid segments corresponding to an arm connected to the hand. Accordingly, the phrase "musculoskeletal representation associated with a hand" should be understood to include both musculoskeletal representations of the hand and/or musculoskeletal representations that include a representation of the hand and at least a portion of an arm connected to the hand.

Figure 7:
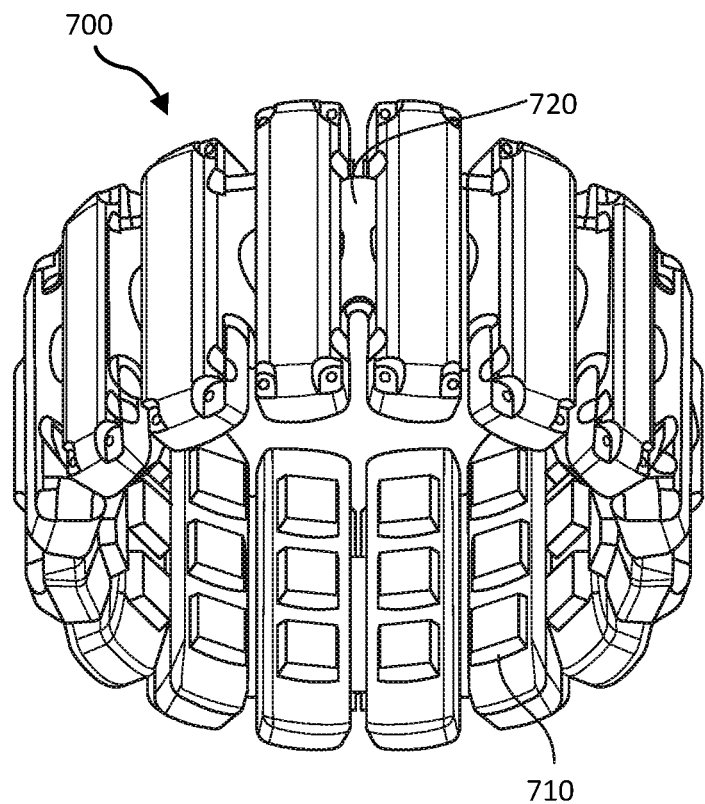
FIG. 7 is an illustration of a perspective view of an example wearable device with sensors, in accordance with embodiments of the present disclosure.

FIG. 7 illustrates a perspective view of an example wearable device 700 that includes sixteen sensors 710 (e.g., EMG sensors) arranged circumferentially around an elastic band 720 configured to be worn around a body part of a user (e.g., a user's lower arm or wrist). As shown, sensors 710 may be arranged circumferentially around elastic band 720. Any suitable number of sensors 710 may be used. The number and arrangement of sensors 710 may depend on the particular application for which the wearable device is used. For example, a wearable armband or wristband may be used to generate control information for controlling an artificial-reality system, a robot, a vehicle, scrolling through text, controlling a virtual avatar, or any other suitable control task.

In some examples, sensors 710 may include a set of neuromuscular sensors (e.g., EMG sensors). In other embodiments, sensors 710 may include a set of neuromuscular sensors and at least one "auxiliary" sensor configured to record (e.g., periodically, continuously, or on demand) auxiliary signals. Examples of auxiliary sensors may include, without limitation, other sensors such as IMU sensors, microphones, imaging sensors (e.g., a camera), radiation-based sensors, laser-scanning devices, or other types of sensors such as a heart-rate monitor.

In some examples, the output of one or more of the sensing components (e.g., sensors 710) may be processed using hardware signal processing circuitry (e.g., to perform amplification, filtering, and/or rectification). In some examples, at least some signal processing of the output of the sensing components may be performed in software. Thus, signal processing of signals sampled by the sensors may be performed in hardware, software, or by any suitable combination of hardware and software, as aspects of the technology described herein are not limited in this respect. Non-limiting examples of a signal processing system used to process data recorded from sensors 710 are discussed in more detail below in reference to FIG. 8.

Figure 8:
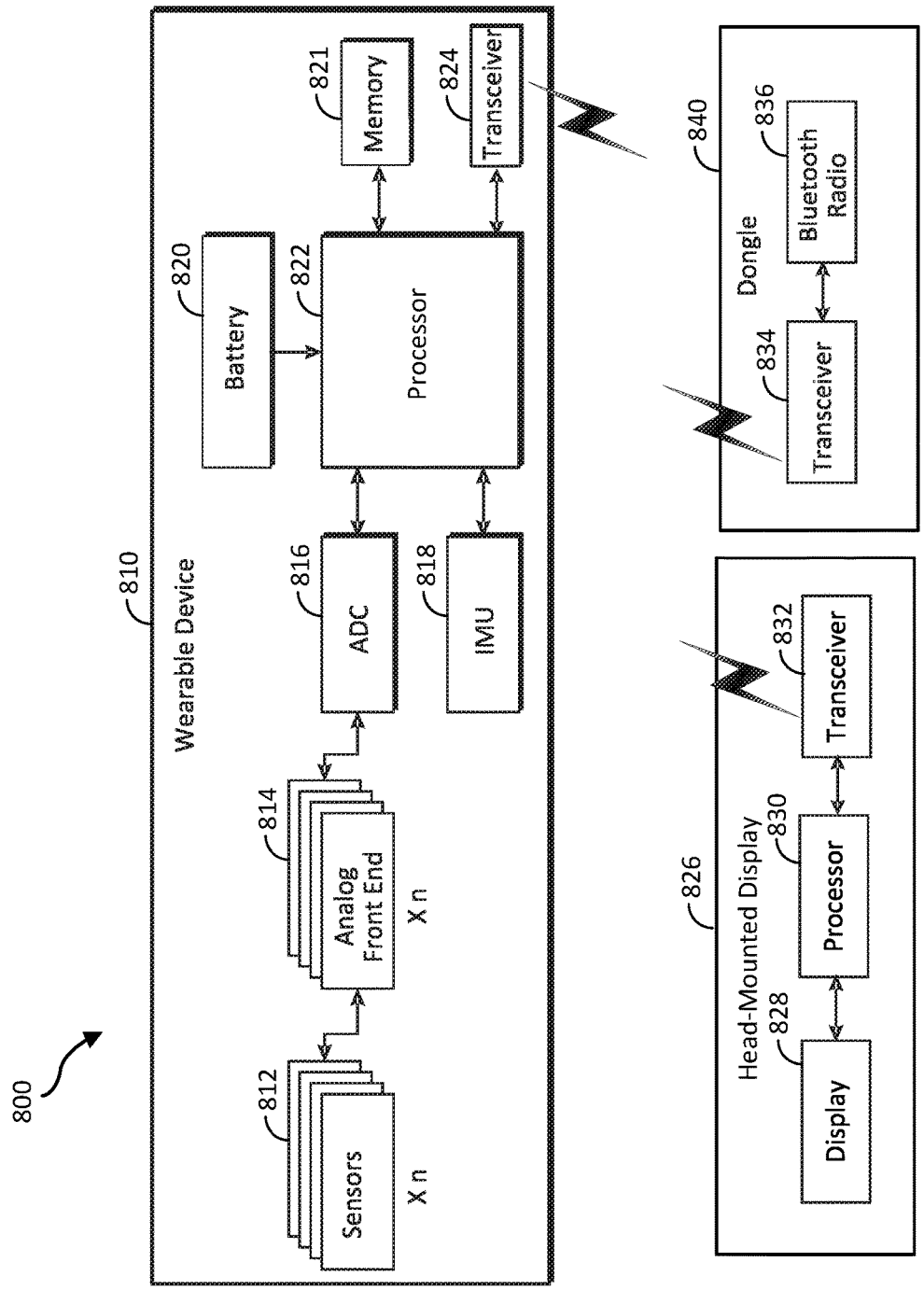
FIG. 8 is an illustration of an example block diagram of a wearable device and a head-mounted display, in accordance with embodiments of the present disclosure.

FIG. 8 illustrates an example block diagram of a wearable system 800 with multiple sensors, in accordance with embodiments of the present disclosure. As shown in FIG. 8, wearable system 800 may include a wearable device 810, a head-mounted display (HMD) 826 and a dongle 840. Wearable device 810, HMD 826, and dongle 840 may communicate to each other via wireless communication (e.g., via Bluetooth™ or other suitable short-range wireless communication technology) or wired communication. Wearable device 810 may include sensors 812 (e.g., EMG sensors), examples of which are described above in reference to FIGS. 5 and 6. Data from sensors 812 and/or data from sensors of HMD 826 may be used to generate the ground truth data (e.g., label time series data). The output of sensors 812 may be provided to analog front end 814 that may be configured to perform analog signal processing (e.g., noise reduction, filtering, amplification, etc.) on the recorded signals from sensors 812. The processed analog signals from analog front end 814 may be provided to analog-to-digital converter (ADC) 816, which may convert the analog signals to digital signals so that the signals may be processed by processor 822 and/or processor 830 of HMD 826.

Processor 822 and/or processor 830 (e.g., a microcontroller, a central processing unit, a digital signal processor, a graphics processor, etc.) may execute instructions stored in memory 821 that implement the methods of the present disclosure including, without limitation, generating one or more training datasets by time-shifting neuromuscular activity time series data and/or label time series data received from sensors 812 by one or more time intervals, training one or more inferential models based on the neuromuscular activity time series data using the one or more training datasets, and configuring a state prediction system to predict the body part state of a user using the trained inferential models. As shown in FIG. 8, processor 822 may also receive inputs from other sensors (e.g., IMU sensor 818, an image sensor, etc.) that may be configured to track a position of a body part of the user. Power may be provided to processor 822 and the other electronic components of wearable device 810 by battery 820. The output of the signal processing performed by processor 822 (e.g., a musculoskeletal representation of the user's body) may be provided to transceiver 824 for transmission to dongle 840 and/or HMD 826.

Dongle 840 may include transceiver 834 configured to communicate with transceiver 824 of wearable device 810 and/or transceiver 832 of HMD 826. Communication between transceivers 834, 824, and 828 may use any suitable wireless technology and protocol, non-limiting examples of which include WiFi, Near Field Communication, and/or Bluetooth™ Bluetooth™ radio 836 may be configured to act as a gateway device to coordinate communication among various wearable devices of system 800 including HMD 826 and wearable device 810. In additional embodiments, wearable device 810, HMD 826, and/or dongle 840 may communicate with each other via a wired connection.

Signals received from sensors 812 may be processed using inferential model(s) as described above to predict a body part state of the user's body. HMD 826 may receive the body part state from wearable device 810 and/or instructions executed on processor 830 of HMD 826 may determine the body part state using the trained one or more inferential models. Processor 830 of HMD 826 may generate a visual representation of the body part state of a user of wearable device 810 using the determined body part state. The visual representation of the user's body part state may be displayed to the user on display 828 of HMD 826. The visual representation of the user's body part state displayed to the user wearing HMD 826 may be in conjunction with an artificial-reality application. In some examples, HMD 826 may be eyewear device 1102 of FIG. 11, virtual-reality system 1200 of FIG. 12, HMD 1402 of FIG. 14, or augmented-reality glasses 1520 of FIG. 15

Figure 9:
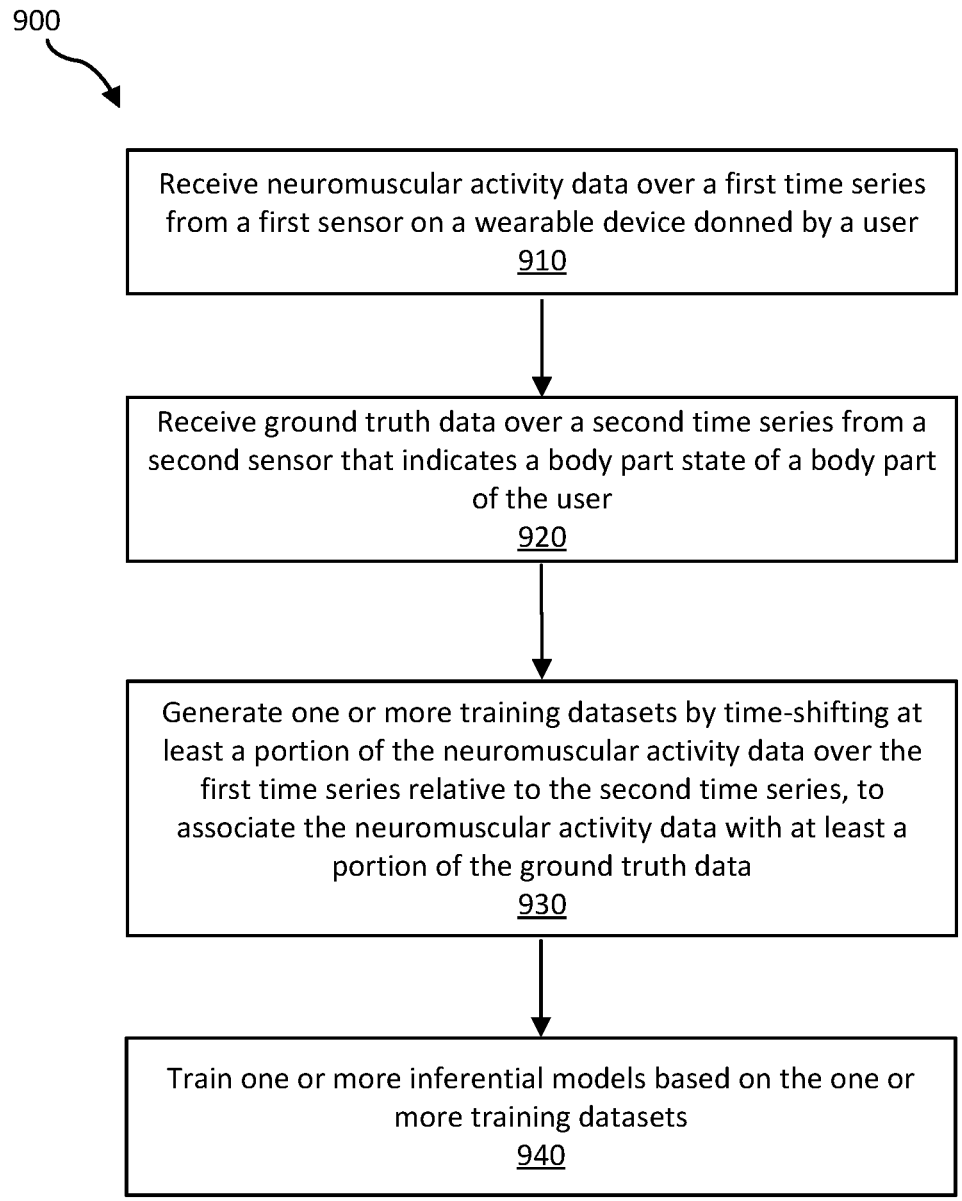
FIG. 9 is an illustration of a flowchart of an example method for predicting a body state based on neuromuscular data, in accordance with embodiments of the present disclosure.

FIG. 9 is a flow diagram illustrating an example method 900 of predicting a body state based on neuromuscular data. At operation 910, method 900 may include receiving neuromuscular activity data over a first time series from a first sensor on a wearable device donned by a user. Operation 910 may be performed in a variety of ways, for example, neuromuscular sensors of a wearable device may periodically generate time series data that indicates neuromuscular activity of the user.

At operation 920, method 900 may include receiving ground truth data from a second, different sensor that indicates a body part state of a body part of the user over a second time series. Operation 920 may be performed in a variety of ways. For example, the ground truth data may be label time series data that indicates a body part state of the user as the user performs a task. The body part state may be or include position information corresponding to the spatial position of different body segments of the user during performance of the task. The position information may be obtained using one or more external devices (e.g., a camera, an IMU) that tracks the position of different points on the user's body during performance of the task.

At operation 930, method 900 may include generating one or more training datasets by time-shifting at least a portion of the neuromuscular activity data over the first time series relative to the second time series, to associate the neuromuscular activity data with at least a portion of the ground truth data. Operation 930 may be performed in a variety of ways. For example, an appropriate time interval may be identified by generating multiple training datasets with multiple temporal shifts. The temporal shifts may be different respective time intervals based on factors including electromechanical delay time of the user (e.g., a user's muscle response time) and/or a known characteristic latency of the system. The time shift interval may determine system latency and may be based on the accuracy requirements of the task. For example, a task prioritizing precise movement (e.g., tele-surgery) may accept greater latency in exchange for greater accuracy, while a task prioritizing rapid movement (e.g., a video game) may accept lower accuracy in exchange for lower latency.

At operation 940, method 900 may include training one or more inferential models based on the one or more training datasets. Operation 940 may be performed in a variety of ways. For example, the inferential models may be trained using a sequence of data sets as input, and each of the data sets in the sequence may include an n-dimensional vector of sensor data (e.g., sensor data from neuromuscular sensors, IMU sensors, etc.). The inferential model may provide output that indicates, for each task or movement performed by a user, the likelihood that the musculoskeletal representation of the user's body will be characterized by a set of musculoskeletal position characteristics. The inferential model may be used to predict body states and create a musculoskeletal representation associated with body parts of a user. A visual representation of the body part of the user may be displayed to the user. For example, a visual representation of the body part of the user may be displayed to the user on a head-mounted display.

Accordingly, the present disclosure includes systems, methods, and apparatuses that may be employed to predict a body part state of a user. For example, an artificial-reality system may include a wearable device(s) that includes sensors and systems configured to predict a body part state of the user. A virtual representation of the predicted state of the body part (e.g., a hand) may be displayed to the user on an HMD. The HMD may also display a virtual object (e.g., a game controller, a sports object) being held by the virtual representation of the hand. The virtual representation of the predicted state of the body part displayed to the user in connection with audio/video content of an artificial-reality application may create a more compelling artificial-reality experience compared to conventional systems, such as by reducing a latency between predicted and actual body movements.

The above-described embodiments may be implemented in any of numerous ways. For example, the embodiments may be implemented using hardware, software or a combination thereof. When implemented in software, the software code may be executed on any suitable processor or collection of processors, whether provided in a single computer or distributed among multiple computers. It should be appreciated that any component or collection of components that perform the functions described above may be generically considered as one or more controllers that control the above-discussed functions. The one or more controllers may be implemented in numerous ways, such as with dedicated hardware or with one or more processors programmed using microcode or software to perform the functions recited above.

In this respect, it should be appreciated that one implementation of the embodiments of the present invention includes at least one non-transitory computer-readable storage medium (e.g., a computer memory, a portable memory, a compact disk, etc.) encoded with a computer program (e.g., a plurality of instructions), which, when executed on a processor, performs the above-discussed functions of the embodiments of the present invention. The computer-readable storage medium may be transportable such that the program stored thereon may be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that may be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Embodiments of the present disclosure may include or be implemented in conjunction with various types of artificial-reality systems. Artificial reality is a form of reality that has been adjusted in some manner before presentation to a user, which may include, e.g., a virtual reality, an augmented reality, a mixed reality, a hybrid reality, or some combination and/or derivative thereof. Artificial-reality content may include completely generated content or generated content combined with captured (e.g., real-world) content. The artificial-reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, e.g., create content in an artificial reality and/or are otherwise used in (e.g., to perform activities in) an artificial reality.

Artificial-reality systems may be implemented in a variety of different form factors and configurations. Some artificial-reality systems may be designed to work without near-eye displays (NEDs). Other artificial-reality systems may include an NED that also provides visibility into the real world (e.g., augmented-reality system 1000 in FIG. 10) or that visually immerses a user in an artificial reality (e.g., virtual-reality system 1100 in FIG. 11). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Figure 10:
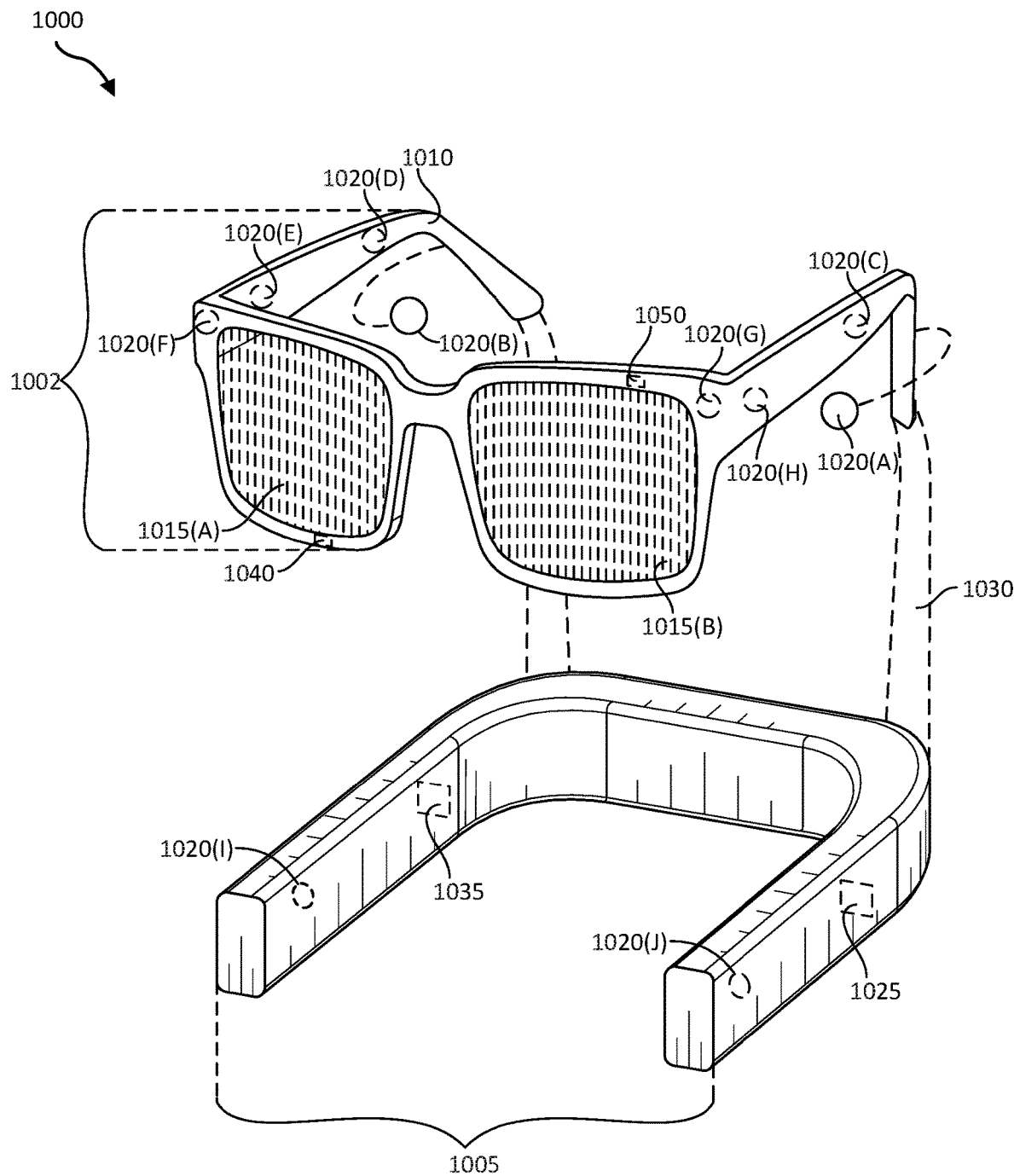
FIG. 10 is an illustration of example augmented-reality glasses that may be used in connection with embodiments of this disclosure.

The embodiments discussed in this disclosure may also be implemented in augmented-reality systems that include one or more NEDs. For example, as shown in FIG. 10, augmented-reality system 1000 may include an eyewear device 1002 with a frame 1010 configured to hold a left display device 1015(A) and a right display device 1015(B) in front of a user's eyes. Display devices 1015(A) and 1015(B) may act together or independently to present an image or series of images to a user. While augmented-reality system 1000 includes two displays, embodiments of this disclosure may be implemented in augmented-reality systems with a single NED or more than two NEDs.

In some embodiments, augmented-reality system 1000 may include one or more sensors, such as sensor 1040. Sensor 1040 may generate measurement signals in response to motion of augmented-reality system 1000 and may be located on substantially any portion of frame 1010. Sensor 1040 may represent a position sensor, an inertial measurement unit (IMU), a depth camera assembly, or any combination thereof. In some embodiments, augmented-reality system 1000 may or may not include sensor 1040 or may include more than one sensor. In embodiments in which sensor 1040 includes an IMU, the IMU may generate calibration data based on measurement signals from sensor 1040. Examples of sensor 1040 may include, without limitation, accelerometers, gyroscopes, magnetometers, other suitable types of sensors that detect motion, sensors used for error correction of the IMU, or some combination thereof.

Augmented-reality system 1000 may also include a microphone array with a plurality of acoustic transducers 1020(A)-1020(J), referred to collectively as acoustic transducers 1020. Acoustic transducers 1020 may be transducers that detect air pressure variations induced by sound waves. Each acoustic transducer 1020 may be configured to detect sound and convert the detected sound into an electronic format (e.g., an analog or digital format). The microphone array in FIG. 10 may include, for example, ten acoustic transducers: 1020(A) and 1020(B), which may be designed to be placed inside a corresponding ear of the user, acoustic transducers 1020(C), 1020(D), 1020(E), 1020(F), 1020(G), and 1020(H), which may be positioned at various locations on frame 1010, and/or acoustic transducers 1020(1) and 1020(J), which may be positioned on a corresponding neckband 1005.

In some embodiments, one or more of acoustic transducers 1020(A)-(F) may be used as output transducers (e.g., speakers). For example, acoustic transducers 1020(A) and/ or 1020(B) may be earbuds or any other suitable type of headphone or speaker.

The configuration of acoustic transducers 1020 of the microphone array may vary. While augmented-reality system 1000 is shown in FIG. 10 as having ten acoustic transducers 1020, the number of acoustic transducers 1020 may be greater or less than ten. In some embodiments, using higher numbers of acoustic transducers 1020 may increase the amount of audio information collected and/or the sensitivity and accuracy of the audio information. In contrast, using a lower number of acoustic transducers 1020 may decrease the computing power required by an associated controller 1050 to process the collected audio information. In addition, the position of each acoustic transducer 1020 of the microphone array may vary. For example, the position of an acoustic transducer 1020 may include a defined position on the user, a defined coordinate on frame 1010, an orientation associated with each acoustic transducer 1020, or some combination thereof.

Acoustic transducers 1020(A) and 1020(B) may be positioned on different parts of the user's ear, such as behind the pinna or within the auricle or fossa. Or, there may be additional acoustic transducers 1020 on or surrounding the ear in addition to acoustic transducers 1020 inside the ear canal. Having an acoustic transducer 1020 positioned next to an ear canal of a user may enable the microphone array to collect information on how sounds arrive at the ear canal. By positioning at least two of acoustic transducers 1020 on either side of a user's head (e.g., as binaural microphones), augmented-reality device 1000 may simulate binaural hearing and capture a 3D stereo sound field around about a user's head. In some embodiments, acoustic transducers 1020(A) and 1020(B) may be connected to augmented-reality system 1000 via a wired connection 1030, and in other embodiments, acoustic transducers 1020(A) and 1020(B) may be connected to augmented-reality system 1000 via a wireless connection (e.g., a Bluetooth connection). In still other embodiments, acoustic transducers 1020(A) and 1020(B) may not be used at all in conjunction with augmented-reality system 1000.

Acoustic transducers 1020 on frame 1010 may be positioned along the length of the temples, across the bridge, above or below display devices 1015(A) and 1015(B), or some combination thereof. Acoustic transducers 1020 may be oriented such that the microphone array is able to detect sounds in a wide range of directions surrounding the user wearing augmented-reality system 1000. In some embodiments, an optimization process may be performed during manufacturing of augmented-reality system 1000 to determine relative positioning of each acoustic transducer 1020 in the microphone array.

In some examples, augmented-reality system 1000 may include or be connected to an external device (e.g., a paired device), such as a neckband 1005. Neckband 1005 generally represents any type or form of paired device. Thus, the following discussion of neckband 1005 may also apply to various other paired devices, such as charging cases, smart watches, smart phones, wrist bands, other wearable devices, hand-held controllers, tablet computers, laptop computers and other external compute devices, etc.

As shown, neckband 1005 may be coupled to eyewear device 1002 via one or more connectors. The connectors may be wired or wireless and may include electrical and/or non-electrical (e.g., structural) components. In some cases, eyewear device 1002 and neckband 1005 may operate independently without any wired or wireless connection between them. While FIG. 10 illustrates the components of eyewear device 1002 and neckband 1005 in example locations on eyewear device 1002 and neckband 1005, the components may be located elsewhere and/or distributed differently on eyewear device 1002 and/or neckband 1005. In some embodiments, the components of eyewear device 1002 and neckband 1005 may be located on one or more additional peripheral devices paired with eyewear device 1002, neckband 1005, or some combination thereof.

Pairing external devices, such as neckband 1005, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 1000 may be provided by a paired device or shared between a paired device and an eyewear device, thus reducing the weight, heat profile, and form factor of the eyewear device overall while still retaining desired functionality. For example, neckband 1005 may allow components that would otherwise be included on an eyewear device to be included in neckband 1005 since users may tolerate a heavier weight load on their shoulders than they would tolerate on their heads. Neckband 1005 may also have a larger surface area over which to diffuse and disperse heat to the ambient environment. Thus, neckband 1005 may allow for greater battery and computation capacity than might otherwise have been possible on a standalone eyewear device. Since weight carried in neckband 1005 may be less invasive to a user than weight carried in eyewear device 1002, a user may tolerate wearing a lighter eyewear device and carrying or wearing the paired device for greater lengths of time than a user would tolerate wearing a heavy standalone eyewear device, thereby enabling users to more fully incorporate artificial-reality environments into their day-to-day activities.

Neckband 1005 may be communicatively coupled with eyewear device 1002 and/or to other devices. These other devices may provide certain functions (e.g., tracking, localizing, depth mapping, processing, storage, etc.) to augmented-reality system 1000. In the embodiment of FIG. 10, neckband 1005 may include two acoustic transducers (e.g., 1020(1) and 1020(J)) that are part of the microphone array (or potentially form their own microphone subarray). Neckband 1005 may also include a controller 1025 and a power source 1035.

Acoustic transducers 1020(1) and 1020(J) of neckband 1005 may be configured to detect sound and convert the detected sound into an electronic format (analog or digital). In the embodiment of FIG. 10, acoustic transducers 1020(1) and 1020(J) may be positioned on neckband 1005, thereby increasing the distance between neckband acoustic transducers 1020(1) and 1020(J) and other acoustic transducers 1020 positioned on eyewear device 1002. In some cases, increasing the distance between acoustic transducers 1020 of the microphone array may improve the accuracy of beamforming performed via the microphone array. For example, if a sound is detected by acoustic transducers 1020(C) and 1020(D) and the distance between acoustic transducers 1020(C) and 1020(D) is greater than, e.g., the distance between acoustic transducers 1020(D) and 1020(E), the determined source location of the detected sound may be more accurate than if the sound had been detected by acoustic transducers 1020(D) and 1020(E).

Controller 1025 of neckband 1005 may process information generated by the sensors on neckband 1005 and/or augmented-reality system 1000. For example, controller 1025 may process information from the microphone array that describes sounds detected by the microphone array. For each detected sound, controller 1025 may perform a direction-of-arrival (DOA) estimation to estimate a direction from which the detected sound arrived at the microphone array. As the microphone array detects sounds, controller 1025 may populate an audio data set with the information. In embodiments in which augmented-reality system 1000 includes an inertial measurement unit, controller 1025 may compute all inertial and spatial calculations from the IMU located on eyewear device 1002. A connector may convey information between augmented-reality system 1000 and neckband 1005 and between augmented-reality system 1000 and controller 1025. The information may be in the form of optical data, electrical data, wireless data, or any other transmittable data form. Moving the processing of information generated by augmented-reality system 1000 to neckband 1005 may reduce weight and heat in eyewear device 1002, making it more comfortable to the user.

A power source 1035 in neckband 1005 may provide power to eyewear device 1002 and/or to neckband 1005. Power source 1035 may include, without limitation, lithium ion batteries, lithium-polymer batteries, primary lithium batteries, alkaline batteries, or any other form of power storage. In some cases, power source 1035 may be a wired power source. Including power source 1035 on neckband 1005 instead of on eyewear device 1002 may help better distribute the weight and heat generated by power source 1035.

As noted, some artificial-reality systems may, instead of blending an artificial reality with actual reality, substantially replace one or more of a user's sensory perceptions of the real world with a virtual experience. One example of this type of system is a head-worn display system, such as virtual-reality system 1100 in FIG. 11, that mostly or completely covers a user's field of view. Virtual-reality system 1100 may include a front rigid body 1102 and a band 1104 shaped to fit around a user's head. Virtual-reality system 1100 may also include output audio transducers 1106(A) and 1106(B). Furthermore, while not shown in FIG. 11, front rigid body 1102 may include one or more electronic elements, including one or more electronic displays, one or more inertial measurement units (IMUS), one or more tracking emitters or detectors, and/or any other suitable device or system for creating an artificial reality experience.

Artificial-reality systems may include a variety of types of visual feedback mechanisms. For example, display devices in augmented-reality system 1000 and/or virtual-reality system 1100 may include one or more liquid crystal displays (LCDs), light-emitting diode (LED) displays, organic LED (OLED) displays, and/or any other suitable type of display screen. Artificial-reality systems may include a single display screen for both eyes or may provide a display screen for each eye, which may allow for additional flexibility for varifocal adjustments or for correcting a user's refractive error. Some artificial-reality systems may also include optical subsystems having one or more lenses (e.g., conventional concave or convex lenses, Fresnel lenses, adjustable liquid lenses, etc.) through which a user may view a display screen.

In addition to or instead of using display screens, some artificial-reality systems may include one or more projection systems. For example, display devices in augmented-reality system 1000 and/or virtual-reality system 1100 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial-reality content and the real world. Artificial-reality systems may also be configured with any other suitable type or form of image projection system.

Artificial-reality systems may also include various types of computer vision components and subsystems. For example, augmented-reality system 1000 and/or virtual-reality system 1100 may include one or more optical sensors, such as two-dimensional (2D) or 3D cameras, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions.

Artificial-reality systems may also include one or more input and/or output audio transducers. In the examples shown in FIG. 11, output audio transducers 1106(A) and 1106(B) may include voice coil speakers, ribbon speakers, electrostatic speakers, piezoelectric speakers, bone conduction transducers, cartilage conduction transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

Figure 11:
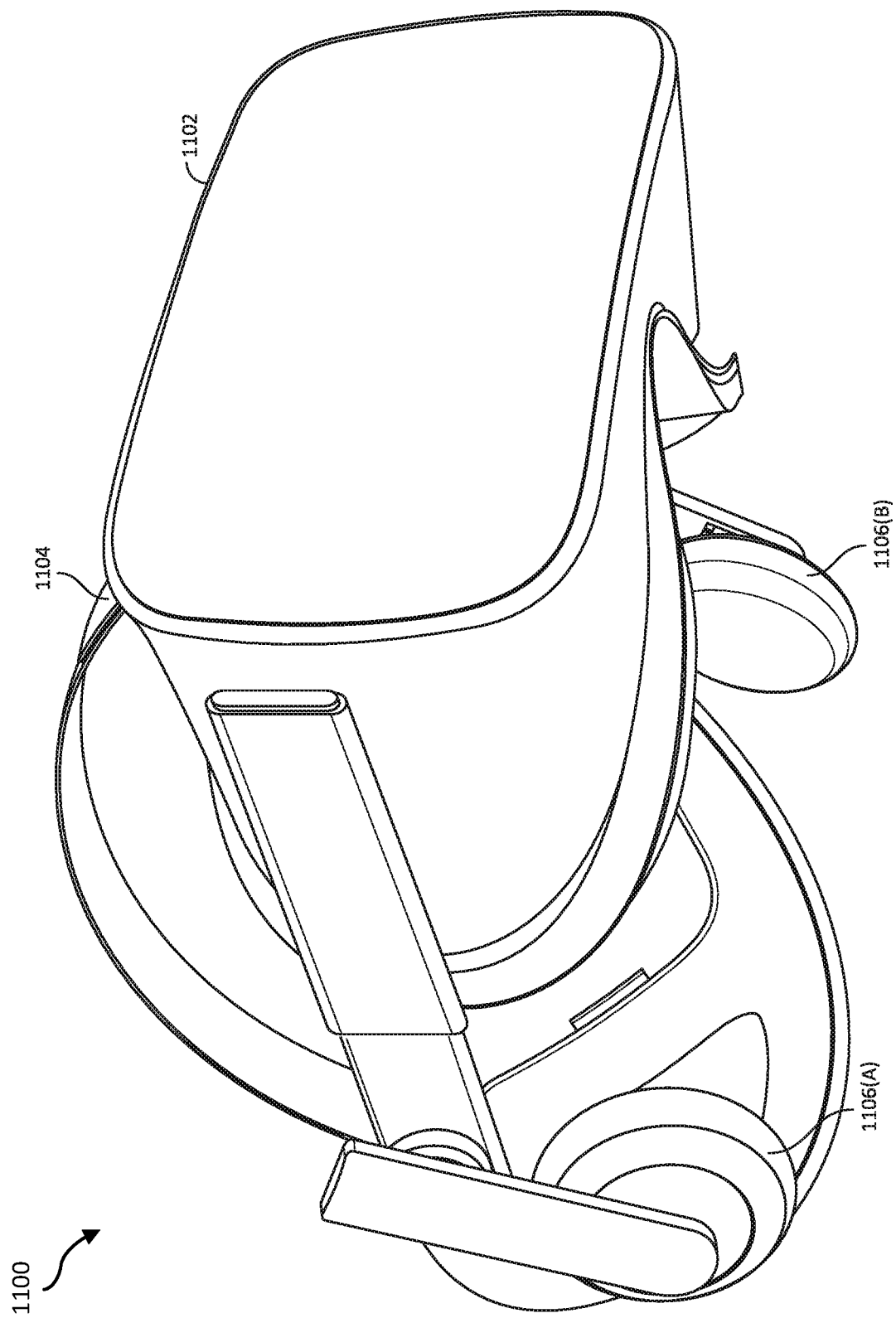
FIG. 11 is an illustration of an example virtual-reality headset that may be used in connection with embodiments of this disclosure.

While not shown in FIG. 11, artificial-reality systems may include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial-reality devices, within other artificial-reality devices, and/or in conjunction with other artificial-reality devices.

By providing haptic sensations, audible content, and/or visual content, artificial-reality systems may create an entire virtual experience or enhance a user's real-world experience in a variety of contexts and environments. For instance, artificial-reality systems may assist or extend a user's perception, memory, or cognition within a particular environment. Some systems may enhance a user's interactions with other people in the real world or may enable more immersive interactions with other people in a virtual world. Artificial-reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visuals aids, etc.). The embodiments disclosed herein may enable or enhance a user's artificial-reality experience in one or more of these contexts and environments and/or in other contexts and environments.

As noted, artificial-reality systems 1000 and 1100 may be used with a variety of other types of devices to provide a more compelling artificial-reality experience. These devices may be haptic interfaces with transducers that provide haptic feedback and/or that collect haptic information about a user's interaction with an environment. The artificial-reality systems disclosed herein may include various types of haptic interfaces that detect or convey various types of haptic information, including tactile feedback (e.g., feedback that a user detects via nerves in the skin, which may also be referred to as cutaneous feedback) and/or kinesthetic feedback (e.g., feedback that a user detects via receptors located in muscles, joints, and/or tendons).

Figure 12:
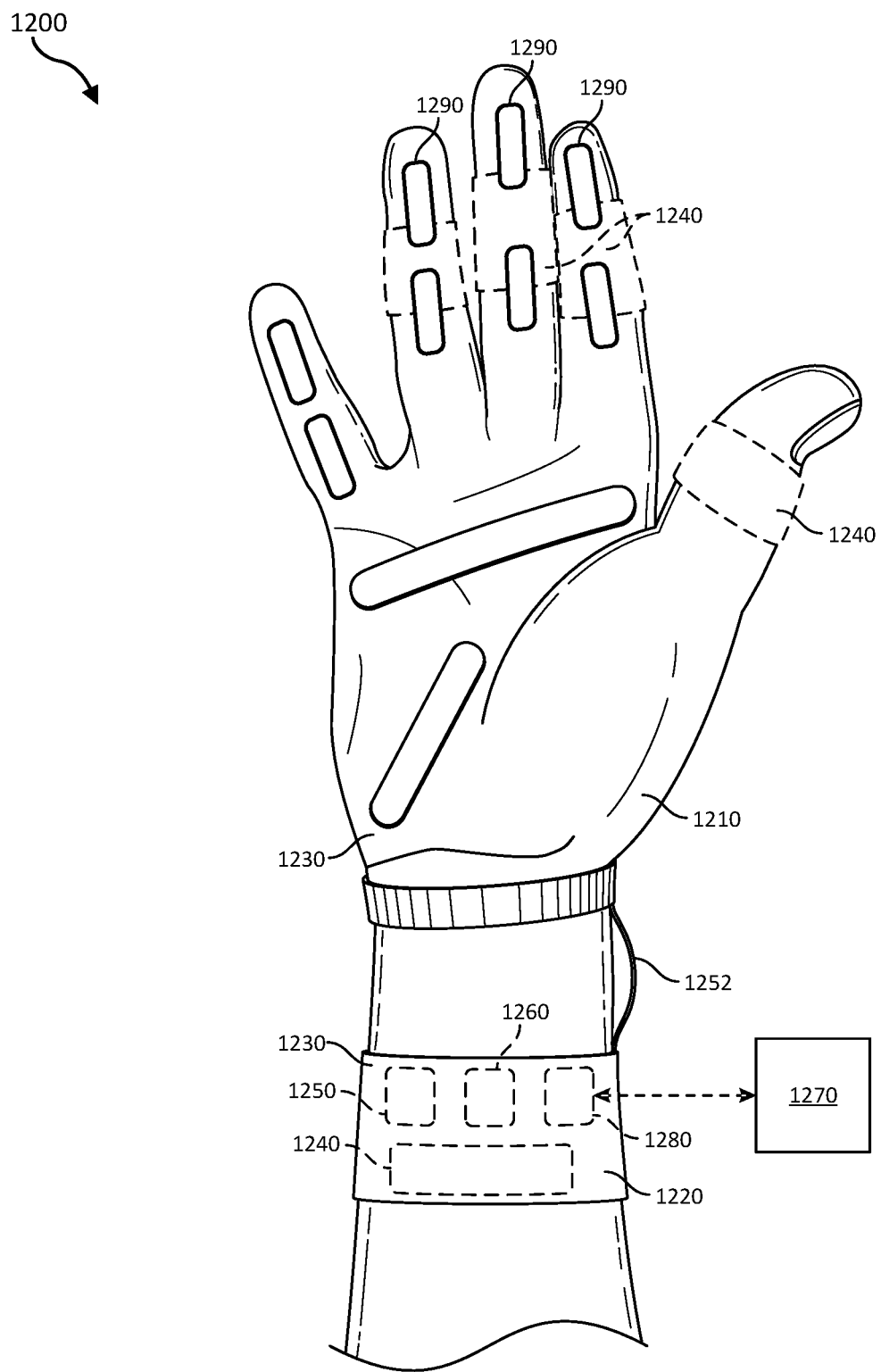
FIG. 12 is an illustration of example haptic devices that may be used in connection with embodiments of this disclosure.

Haptic feedback may be provided by interfaces positioned within a user's environment (e.g., chairs, tables, floors, etc.) and/or interfaces on articles that may be worn or carried by a user (e.g., gloves, wristbands, etc.). As an example, FIG. 12 illustrates a vibrotactile system 1200 in the form of a wearable glove (haptic device 1210) and wristband (haptic device 1220). Haptic device 1210 and haptic device 1220 are shown as examples of wearable devices that include a flexible, wearable textile material 1230 that is shaped and configured for positioning against a user's hand and wrist, respectively. This disclosure also includes vibrotactile systems that may be shaped and configured for positioning against other human body parts, such as a finger, an arm, a head, a torso, a foot, or a leg. By way of example and not limitation, vibrotactile systems according to various embodiments of the present disclosure may also be in the form of a glove, a headband, an armband, a sleeve, a head covering, a sock, a shirt, or pants, among other possibilities. In some examples, the term "textile" may include any flexible, wearable material, including woven fabric, non-woven fabric, leather, cloth, a flexible polymer material, a composite material, etc.

One or more vibrotactile devices 1240 may be positioned at least partially within one or more corresponding pockets formed in textile material 1230 of vibrotactile system 1200. Vibrotactile devices 1240 may be positioned in locations to provide a vibrating sensation (e.g., haptic feedback) to a user of vibrotactile system 1200. For example, vibrotactile devices 1240 may be positioned to be against the user's finger(s), thumb, or wrist, as shown in FIG. 12. Vibrotactile devices 1240 may, in some examples, be sufficiently flexible to conform to or bend with the user's corresponding body part(s).

A power source 1250 (e.g., a battery) for applying a voltage to vibrotactile devices 1240 for activation thereof may be electrically coupled to vibrotactile devices 1240, such as via conductive wiring 1252. In some examples, each of vibrotactile devices 1240 may be independently electrically coupled to power source 1250 for individual activation. In some embodiments, a processor 1260 may be operatively coupled to power source 1250 and configured (e.g., programmed) to control activation of vibrotactile devices 1240.

Vibrotactile system 1200 may be implemented in a variety of ways. In some examples, vibrotactile system 1200 may be a standalone system with integral subsystems and components for operation independent of other devices and systems. As another example, vibrotactile system 1200 may be configured for interaction with another device or system 1270. For example, vibrotactile system 1200 may, in some examples, include a communications interface 1280 for receiving and/or sending signals to the other device or system 1270. The other device or system 1270 may be a mobile device, a gaming console, an artificial-reality (e.g., virtual-reality, augmented-reality, mixed-reality) device, a personal computer, a tablet computer, a network device (e.g., a modem, a router, etc.), a handheld controller, etc. A communications interface 1280 may enable communications between vibrotactile system 1200 and the other device or system 1270 via a wireless (e.g., Wi-Fi, Bluetooth, cellular, radio, etc.) link or a wired link. If present, communications interface 1280 may be in communication with processor 1260, such as to provide a signal to processor 1260 to activate or deactivate one or more of vibrotactile devices 1240.

Vibrotactile system 1200 may optionally include other subsystems and components, such as touch-sensitive pads 1290, pressure sensors, motion sensors, position sensors, lighting elements, and/or user interface elements (e.g., an on/off button, a vibration control element, etc.). During use, vibrotactile devices 1240 may be configured to be activated for a variety of different reasons, such as in response to the user's interaction with user interface elements, a signal from the motion or position sensors, a signal from touch-sensitive pads 1290, a signal from the pressure sensors, a signal from the other device or system 1270, etc.

Although power source 1250, processor 1260, and communications interface 1280 are illustrated in FIG. 12 as being positioned in haptic device 1220, the present disclosure is not so limited. For example, one or more of power source 1250, processor 1260, or communications interface 1280 may be positioned within haptic device 1210 or within another wearable textile.

Figure 13:
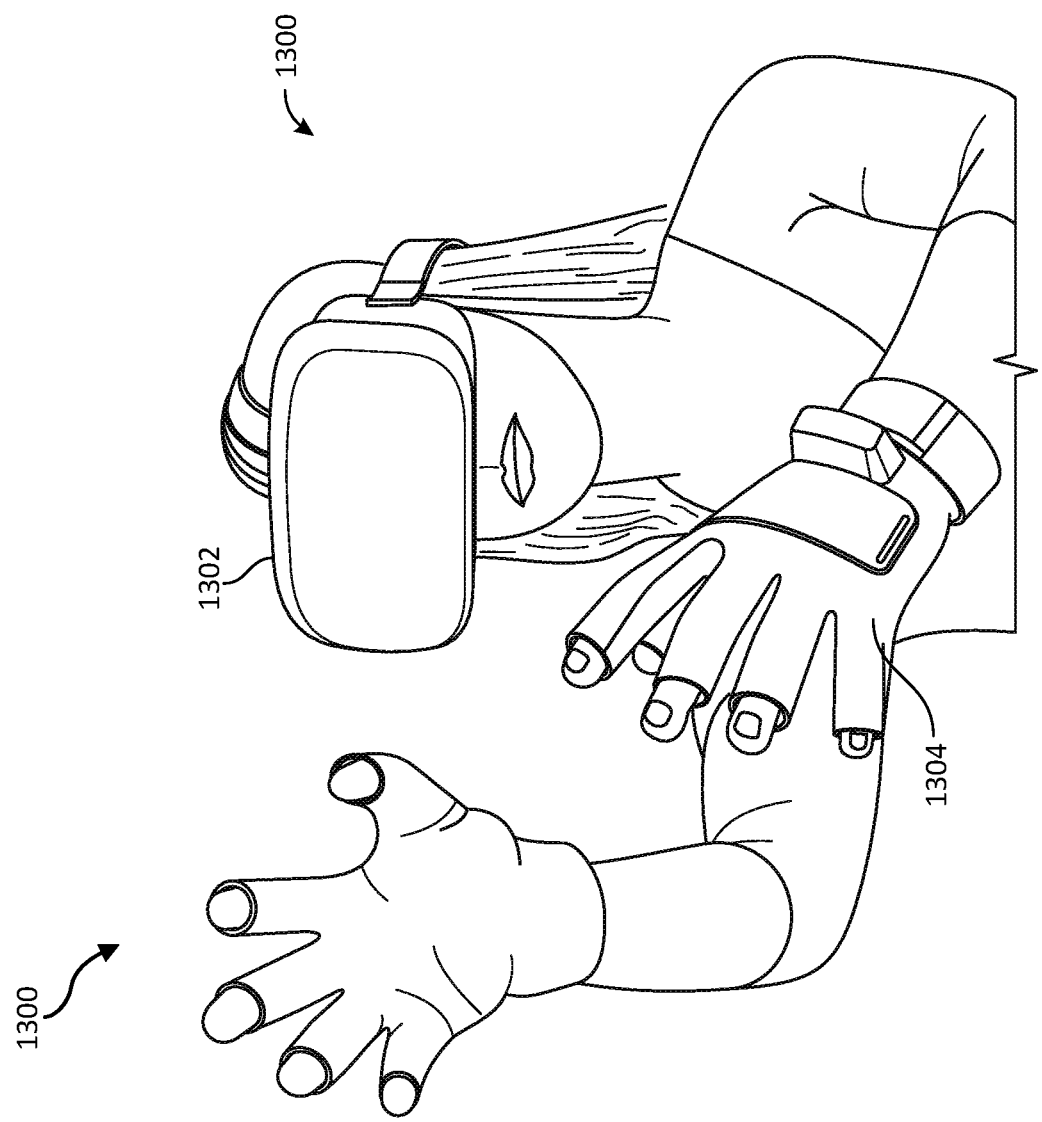
FIG. 13 is an illustration of an example virtual-reality environment according to embodiments of this disclosure.

Haptic wearables, such as those shown in and described in connection with FIG. 12, may be implemented in a variety of types of artificial-reality systems and environments. FIG. 13 shows an example artificial-reality environment 1300 including one head-mounted virtual-reality display and two haptic devices (i.e., gloves), and in other embodiments any number and/or combination of these components and other components may be included in an artificial-reality system. For example, in some embodiments there may be multiple head-mounted displays each having an associated haptic device, with each head-mounted display and each haptic device communicating with the same console, portable computing device, or other computing system.

Head-mounted display 1302 generally represents any type or form of virtual-reality system, such as virtual-reality system 1100 in FIG. 11. Haptic device 1304 generally represents any type or form of wearable device, worn by a use of an artificial-reality system, that provides haptic feedback to the user to give the user the perception that he or she is physically engaging with a virtual object. In some embodiments, haptic device 1304 may provide haptic feedback by applying vibration, motion, and/or force to the user. For example, haptic device 1304 may limit or augment a user's movement. To give a specific example, haptic device

1304 may limit a user's hand from moving forward so that the user has the perception that his or her hand has come in physical contact with a virtual wall. In this specific example, one or more actuators within the haptic advice may achieve the physical-movement restriction by pumping fluid into an inflatable bladder of the haptic device. In some examples, a user may also use haptic device 1304 to send action requests to a console. Examples of action requests include, without limitation, requests to start an application and/or end the application and/or requests to perform a particular action within the application.

Figure 14:
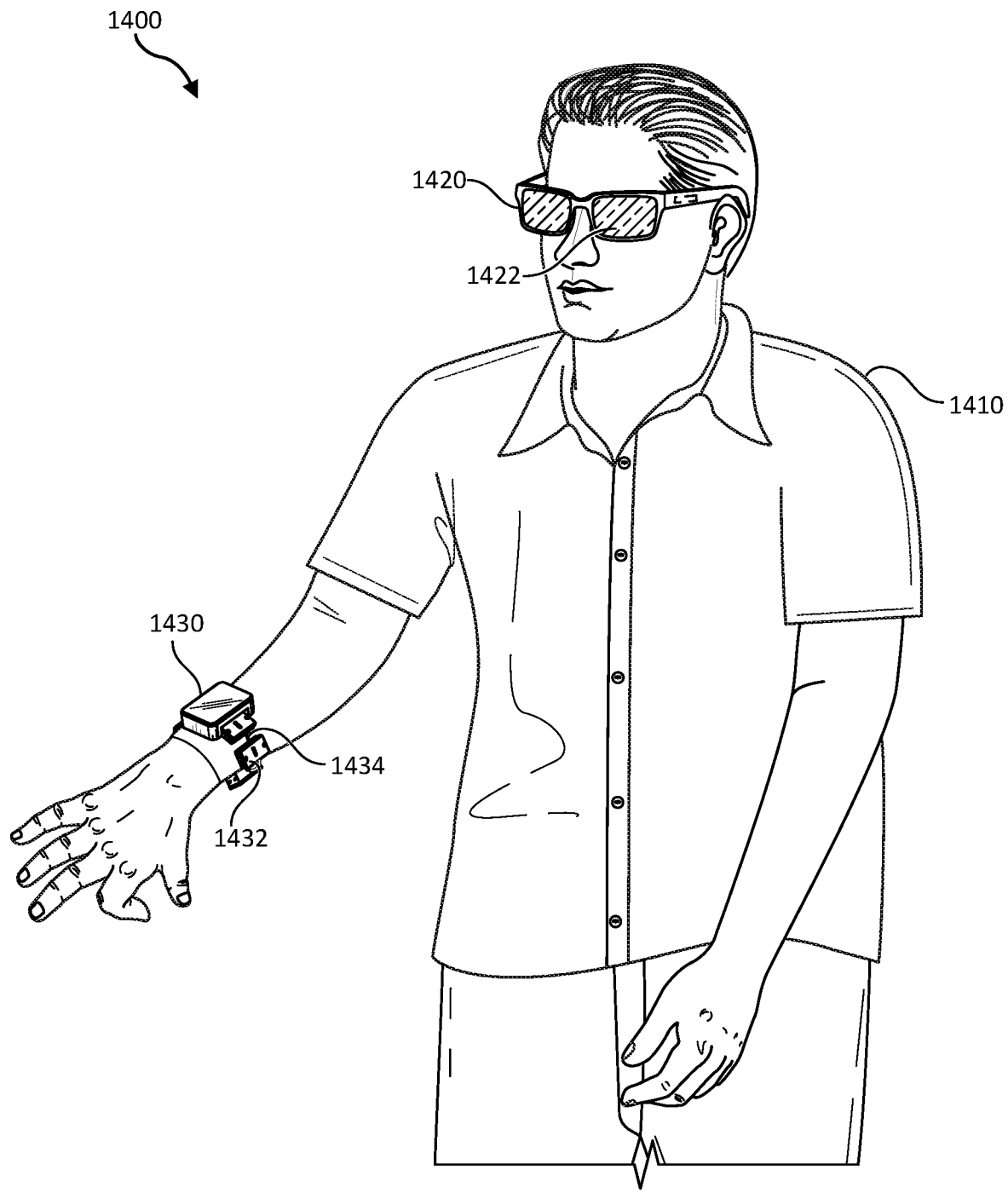
FIG. 14 is an illustration of an example augmented-reality environment according to embodiments of this disclosure.

While haptic interfaces may be used with virtual-reality systems, as shown in FIG. 13, haptic interfaces may also be used with augmented-reality systems, as shown in FIG. 14. FIG. 14 is a perspective view a user 1410 interacting with an augmented-reality system 1400. In this example, user 1410 may wear a pair of augmented-reality glasses 1420 that have one or more displays 1422 and that are paired with a haptic device 1430. Haptic device 1430 may be a wristband that includes a plurality of band elements 1432 and a tensioning mechanism 1434 that connects band elements 1432 to one another.

One or more of band elements 1432 may include any type or form of actuator suitable for providing haptic feedback. For example, one or more of band elements 1432 may be configured to provide one or more of various types of cutaneous feedback, including vibration, force, traction, texture, and/or temperature. To provide such feedback, band elements 1432 may include one or more of various types of actuators. In one example, each of band elements 1432 may include a vibrotactor configured to vibrate in unison or independently to provide one or more of various types of haptic sensations to a user. Alternatively, only a single band element or a subset of band elements may include vibrotactors.

Haptic devices 1210, 1220, 1304, and 1430 may include any suitable number and/or type of haptic transducer, sensor, and/or feedback mechanism. For example, haptic devices 1210, 1220, 1304, and 1430 may include one or more mechanical transducers, piezoelectric transducers, and/or fluidic transducers. Haptic devices 1210, 1220, 1304, and 1430 may also include various combinations of different types and forms of transducers that work together or independently to enhance a user's artificial-reality experience. In one example, each of band elements 1432 of haptic device 1430 may include a vibrotactor (e.g., a vibrotactile actuator) configured to vibrate in unison or independently to provide one or more of various types of haptic sensations to a user.

By way of non-limiting examples, the following embodiments are included in the present disclosure.

Example 1: A method comprising receiving neuromuscular activity data over a first time series from a first sensor on a wearable device donned by a user, receiving ground truth data over a second time series from a second sensor that indicates a body part state of a body part of the user, generating one or more training datasets by time-shifting, at least, a portion of the neuromuscular activity data over the first time series relative to the second time series, to associate the neuromuscular activity data with at least a portion of the ground truth data, and training one or more inferential models based on the one or more training datasets.

Example 2: The method of Example 1, further comprising time-shifting the portion of the neuromuscular activity data by one or more time intervals based on an electromechanical delay associated with a specific body part of the user.

Example 3: The method of Examples 1 or 2, wherein the one or more inferential models comprises multiple inferential models and the method further comprises determining a prediction accuracy for each of the multiple inferential models, selecting a first inferential model from the multiple inferential models based on the determined prediction accuracy for each of the multiple inferential models, and predicting the body part state of the user using the first inferential model.

Example 4: The method of any of Examples 1 through 3, wherein the first inferential model is selected further based on a characteristic latency associated with a specific body part of the user.

Example 5: The method of any of Examples 1 through 4, wherein determining the prediction accuracy for each of the multiple inferential models comprises determining a likelihood of correctly estimating the body part state using each of the multiple inferential models.

Example 6: The method of any of Examples 1 through 5, wherein determining the prediction accuracy for each of the multiple inferential models comprises determining error values between known characteristic latencies associated with the body part state of the user and latencies associated with the body part state of the user that are predicted using each of the multiple inferential models.

Example 7: The method of any of Examples 1 through 6, further comprising predicting the body part state of the user based on the one or more inferential models.

Example 8: The method of any of Examples 1 through 7, further comprising determining that the predicted body part state of the user corresponds to a particular gesture and performing an action in an artificial-reality environment in response to determining that the predicted body part state of the user corresponds to the particular gesture.

Example 9: The method of any of Examples 1 through 8, further comprising determining prediction accuracies for two inferential models of the one or more inferential models, wherein the two inferential models correspond to two different time intervals, determining that the prediction accuracies for the two inferential models satisfy a threshold value, selecting one of the two inferential models corresponding to a greater of the two different time intervals, and predicting the body part state of the user using the selected one of the two inferential models.

Example 10: The method of any of Examples 1 through 9, wherein the threshold value is at least one of an absolute difference in the prediction accuracies for the two inferential models or a relative difference in prediction accuracy between a more accurate one of the two inferential models and a less accurate one of the two inferential models.

Example 11: The method of any of Examples 1 through 10, wherein selecting one of the two inferential models is further based on a task-dependent accuracy level.

Example 12: The method of any of Examples 1 through 11, wherein the is second sensor is part of a head-mounted display and the second sensor comprises at least one of an optical sensor, an inertial measurement sensor, a mutual magnetic induction measurement sensor, or a pressure sensor.

Example 13: The method of any of Examples 1 through 12, wherein the body part state of the user is represented as a binary label indicating a presence or an absence of at least one of a pose or a gesture.

Example 14: The method of any of Examples 1 through 13, wherein the body part state includes at least one of a force associated with the body part, a movement of the body part, a pose associated with the body part, a gesture associated with the body part, or a gesture associated with a portion of the body part.

Example 15: A wearable device, comprising one or more neuromuscular sensors configured to record a plurality of neuromuscular signals from a user donning the wearable device and one or more processors programmed to receive neuromuscular activity data over a time series from the one or more neuromuscular sensors wherein the neuromuscular activity data corresponds to the neuromuscular signals recorded by the one or more neuromuscular sensors, receive position data that indicates a state of a body part of a user over the time series, generate one or more training datasets by time-shifting at least one of the neuromuscular activity data or the position data by one or more time intervals, train one or more inferential models based on at least the one or more training datasets, and predict the user's body part state based on the trained one or more inferential models.

Example 16: The wearable device of Example 15, wherein the one or more processors are further programmed to select the one or more time intervals based on an electromechanical delay associated with the body part of the user.

Example 17: The wearable device of Example 15 or Example 16, wherein the one or more inferential models comprise multiple inferential models and the one or more processors is further programmed to determine a prediction accuracy for each of the multiple inferential models, selecting a first inferential models from the multiple inferential models based on the determined prediction accuracy for each of the multiple inferential models, and predicting the body part state of the user using the first inferential model.

Example 18: The wearable device of any of Examples 15 through 17, wherein the one of the multiple inferential models is selected further based on a characteristic latency of the user's body part.

Example 19: The wearable device of any of Examples 15 through 18, wherein determining the prediction accuracy for each of the multiple inferential models comprises determining a likelihood of correctly estimating a known body part state using each of the multiple inferential models.

Example 20: An artificial-reality system comprising a head-mounted display and a wearable device, comprising one or more neuromuscular sensors configured to record a plurality of neuromuscular signals from a user donning the wearable device, and one or more processors programmed to receive neuromuscular activity data over a time series from the neuromuscular sensors configured to record the plurality of neuromuscular signals, receive position data that indicates a body part state of a body part of the user over the time series, generate one or more training datasets by time-shifting at least one of the neuromuscular activity data or the position data by one or more time intervals, train one or more inferential models based on at least the neuromuscular activity time series data using the one or more training datasets, and predict the body part state of the user using the trained one or more inferential models, wherein the head-mounted display is configured to display a visual representation of the body part of the user.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A method comprising:
    receiving neuromuscular activity data over a first time series from a first sensor on a wearable device donned by a user;
    receiving ground truth data over a second time series from a second sensor that indicates a body part state of a body part of the user;
    generating one or more training datasets by time-shifting, at least, a portion of the neuromuscular activity data over the first time series relative to the second time series, to associate the neuromuscular activity data with at least a portion of the ground truth data; and
    training one or more inferential models based on the one or more training datasets.

2. The method of claim 1, further comprising time-shifting the portion of the neuromuscular activity data by one or more time intervals based on an electromechanical delay associated with a specific body part of the user.

3. The method of claim 1, wherein:
    the one or more inferential models comprise multiple inferential models; and
    the method further comprises:
        determining a prediction accuracy for each of the multiple inferential models;
        selecting a first inferential model from the multiple inferential models based on the determined prediction accuracy for each of the multiple inferential models; and
        predicting the body part state of the user using the first inferential model.

4. The method of claim 3, wherein the first inferential model is selected further based on a characteristic latency associated with a specific body part of the user.

5. The method of claim 3, wherein determining the prediction accuracy for each of the multiple inferential models comprises determining a likelihood of correctly estimating the body part state using each of the multiple inferential models.

6. The method of claim 3, wherein determining the prediction accuracy for each of the multiple inferential models comprises determining error values between known characteristic latencies associated with the body part state of the user and latencies associated with the body part state of the user that are predicted using each of the multiple inferential models.

7. The method of claim 1, further comprising predicting the body part state of the user based on the one or more inferential models.

8. The method of claim 7, further comprising:
    determining that the predicted body part state of the user corresponds to a particular gesture; and
    performing an action in an artificial-reality environment in response to determining that the predicted body part state of the user corresponds to the particular gesture.

9. The method of claim 1, further comprising:
determining prediction accuracies for two inferential models of the one or more inferential models, wherein the two inferential models correspond to two different time intervals;
determining that the prediction accuracies for the two inferential models satisfy a threshold value;
selecting one of the two inferential models corresponding to a greater of the two different time intervals; and
predicting the body part state of the user using the selected one of the two inferential models.

10. The method of claim 9, wherein the threshold value is at least one of an absolute difference in the prediction accuracies for the two inferential models or a relative difference in prediction accuracy between a more accurate one of the two inferential models and a less accurate one of the two inferential models.

11. The method of claim 9, wherein selecting one of the two inferential models is further based on a task-dependent accuracy level.

12. The method of claim 1, wherein:
the second sensor is part of a head-mounted display, and
the second sensor comprises at least one of an optical sensor, an inertial measurement sensor, a mutual magnetic induction measurement sensor, or a pressure sensor.

13. The method of claim 1, wherein the body part state of the user is represented as a binary label indicating a presence or an absence of at least one of a pose or a gesture.

14. The method of claim 1, wherein the body part state includes at least one of a force associated with the body part, a movement of the body part, a pose associated with the body part, a gesture associated with the body part, or a gesture associated with a portion of the body part.

15. A wearable device, comprising:
one or more neuromuscular sensors configured to record neuromuscular signals from a user donning the wearable device; and
one or more processors programmed to:
receive neuromuscular activity data over a time series from the one or more neuromuscular sensors, wherein the neuromuscular activity data corresponds to the neuromuscular signals recorded by the one or more neuromuscular sensors;
receive position data that indicates a state of a body part of a user over the time series;
generate one or more training datasets by time-shifting at least one of the neuromuscular activity data or the position data by one or more time intervals;
train one or more inferential models based, at least in part, on the one or more training datasets; and
predict the user's body part state based on the trained one or more inferential models.

16. The wearable device of claim 15, wherein the one or more processors are further programmed to select the one or more time intervals based on an electromechanical delay associated with the body part of the user.

17. The wearable device of claim 15, wherein:
the one or more inferential models comprise multiple inferential models; and
the one or more processors is further programmed to:
determine a prediction accuracy for each of the multiple inferential models;
select a first inferential model from the multiple inferential models based on the determined prediction accuracy for each of the multiple inferential models; and
predict the body part state of the user using the first inferential model.

18. The wearable device of claim 17, wherein the one of the multiple inferential models is selected further based on a characteristic latency of the user's body part.

19. The wearable device of claim 17, wherein determining the prediction accuracy for each of the multiple inferential models comprises determining a likelihood of correctly estimating a known body part state using each of the multiple inferential models.

20. An artificial-reality system comprising:
a head-mounted display; and
a wearable device, comprising:
one or more neuromuscular sensors configured to record a plurality of neuromuscular signals from a user donning the wearable device; and
one or more processors programmed to:
receive neuromuscular activity data over a time series from the neuromuscular sensors configured to record the plurality of neuromuscular signals;
receive position data that indicates a body part state of a body part of the user over the time series;
generate one or more training datasets by time-shifting at least one of the neuromuscular activity data or the position data by one or more time intervals;
train one or more inferential models based on at least the neuromuscular activity time series data using the one or more training datasets; and
predict the body part state of the user using the trained one or more inferential models, wherein:
the head-mounted display is configured to display a visual representation of the body part of the user.

* * * * *